US008909484B2

(12) United States Patent
Farsad et al.

(10) Patent No.: US 8,909,484 B2
(45) Date of Patent: Dec. 9, 2014

(54) AUTOMATED HYDRAULIC PROPERTY MEASUREMENT APPARATUS

(75) Inventors: Ali Farsad, Santa Barbara, CA (US); Thomas G. Macfie, Crawfordville, GA (US); Whitney Skaling, Buellton, CA (US); Gregory T. Hart, Lompoc, CA (US)

(73) Assignee: Soilmoisture Equipment Corp., Goleta, CA (US)

(*) Notice: Subject to any disclaimer, the term of this patent is extended or adjusted under 35 U.S.C. 154(b) by 521 days.

(21) Appl. No.: 13/411,855

(22) Filed: Mar. 5, 2012

(65) Prior Publication Data

US 2013/0080074 A1    Mar. 28, 2013

Related U.S. Application Data

(60) Provisional application No. 61/539,250, filed on Sep. 26, 2011.

(51) Int. Cl.
| | | |
|---|---|---|
| *G06F 19/00* | (2011.01) | |
| *G01N 11/00* | (2006.01) | |
| *G01N 5/02* | (2006.01) | |
| *G01N 33/24* | (2006.01) | |
| *G01N 15/08* | (2006.01) | |

(52) U.S. Cl.
CPC ............... *G01N 11/00* (2013.01); *G06F 19/00* (2013.01); *G01N 5/02* (2013.01); *G01N 33/24* (2013.01); *G01N 15/0893* (2013.01); *G01N 2015/0866* (2013.01)
USPC .......................................................... 702/25

(58) Field of Classification Search
CPC ... B01L 3/5085; B01L 9/06; B01L 2200/142; G01N 2035/0436; A61L 15/225
USPC ........................................... 702/25, 182–185
See application file for complete search history.

(56) References Cited

U.S. PATENT DOCUMENTS

| | | | |
|---|---|---|---|
| 4,884,436 A | 12/1989 | Ankeny et al. | |
| 4,956,993 A | 9/1990 | Mehler | |
| 5,157,959 A | 10/1992 | Ankeny et al. | |
| 2009/0130745 A1* | 5/2009 | Williams et al. ........... | 435/287.2 |
| 2012/0318046 A1* | 12/2012 | Ehrnsperger et al. ............. | 73/38 |

OTHER PUBLICATIONS

Kechavarzi, C., Design of a fully automated tension infiltrometer for unsaturated hydraulic conductivity measurement, retrieved Feb. 1, 2012 from http://www.cranfield.ac.uk/sas/nsri/research/projects/infiltrometer.
Wooding, R. A., Steady infiltration from a shallow circular pond, Water Resources Research, Dec. 1968, vol. 4, No. 6, pp. 1259-1273, American Geophysical Union, Washington, DC.
Soil Measurement Systems, Tension infiltrometer, retrieved Feb. 1, 2012 from http://www.soilmeasurement.com/tension_infil.html.

* cited by examiner

*Primary Examiner* — Edward Raymond
(74) *Attorney, Agent, or Firm* — Lyon & Harr, LLP; Richard T. Lyon

(57) ABSTRACT

An apparatus for testing a porous medium is provided. The apparatus includes a liquid processing subsystem and a liquid weighing subsystem. The liquid processing subsystem is interfaced with the medium in a manner that establishes liquid contact there-between. The liquid processing and liquid weighing subsystems are sealably interconnected via an interconnecting liquid tube. The liquid weighing subsystem stores a liquid which flows therefrom, through the tube, through the liquid processing subsystem, and into the medium until it is saturated with the liquid. The liquid weighing subsystem automatically measures the weight of the liquid stored therein on an ongoing basis and uses these measurements to determine one or more hydraulic properties of the medium.

21 Claims, 6 Drawing Sheets

US 8,909,484 B2

AUTOMATED HYDRAULIC PROPERTY MEASUREMENT APPARATUS

CROSS REFERENCE TO RELATED APPLICATION

This application claims the benefit of and priority to provisional U.S. patent application Ser. No. 61/539,250 filed Sep. 26, 2011.

BACKGROUND

In the arts of soil science and hydrology the hydraulic properties of soils and other porous media are often measured in situ. These measurements are subsequently analyzed in various ways for various purposes such as studying the efficiency of irrigation and drainage, optimizing the availability of water for plants, optimizing the yield of crops, and minimizing erosion. These measurements can also be used to follow the movement of liquids in porous media, model soil pore structure, and predict plant growth and other associated factors.

SUMMARY

This Summary is provided to introduce a selection of concepts, in a simplified form, that are further described hereafter in the Detailed Description. This Summary is not intended to identify key features or essential features of the claimed subject matter, nor is it intended to be used as an aid in determining the scope of the claimed subject matter.

Hydraulic property measurement apparatus embodiments described herein generally involve an apparatus for testing a porous medium. In an exemplary embodiment the apparatus includes a liquid processing subsystem and a liquid weighing subsystem. The liquid processing subsystem is interfaced with the medium in a manner that establishes liquid contact between the liquid processing subsystem and the medium. The liquid processing and liquid weighing subsystems are sealably interconnected via an interconnecting liquid tube. The liquid weighing subsystem stores a liquid which flows from the liquid weighing subsystem, through the tube, through the liquid processing subsystem, and into the medium until the medium is saturated with the liquid. The liquid weighing subsystem automatically measures the weight of the liquid stored therein on an ongoing basis and uses these liquid weight measurements to determine one or more hydraulic properties of the medium.

DESCRIPTION OF THE DRAWINGS

The specific features, aspects, and advantages of the hydraulic property measurement apparatus embodiments (hereafter simply referred to as "apparatus embodiments") described herein will become better understood with regard to the following description, appended claims, and accompanying drawings where:

DETAILED DESCRIPTION

Figure 1:
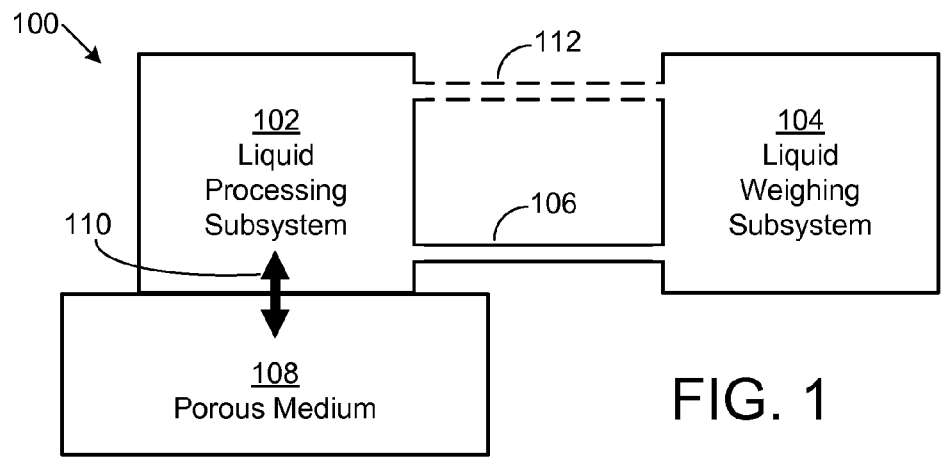
FIG. 1 is a diagram illustrating an exemplary embodiment, in simplified form, of an architectural framework for the apparatus embodiments described herein.

In the following description of hydraulic property measurement apparatus embodiments (hereafter simply referred to as "apparatus embodiments") reference is made to the accompanying drawings which form a part hereof, and in which are shown, by way of illustration, specific embodiments in which the apparatus can be practiced. It is understood that other embodiments can be utilized and structural changes can be made without departing from the scope of the apparatus embodiments. The use of the terms "seal" and "sealably" herein are intended to imply an airtight and liquid tight seal which is capable of maintaining both a low pressure and a partial/moderate vacuum, and also prevents liquid leakage.

1.0 Automated Hydraulic Property Measurement Apparatus

The apparatus embodiments described herein are generally applicable to the testing of a porous medium. By way of example but not limitation, the apparatus embodiments can measure one or more hydraulic properties of a porous medium, where the measurements can be made in situ (e.g., in the field) and in an automated (e.g., unattended) manner. The apparatus embodiments are advantageous for various reasons including, but not limited to, the following.

The apparatus embodiments described herein are operational with a wide variety of different types of porous media such as soils (which may include materials such as clay, silt, sand and organic matter), gravel, wood, rock, and concrete, among others. The apparatus embodiments are also operational with a wide variety of different types of liquids such as water, oil, and any homogenized mixture of different substances in a liquid form, among others. The apparatus embodiments can also be used to measure a wide variety of hydraulic properties of the porous medium, where the measurements can be made quickly, reliably and accurately in a wide variety of environmental conditions using a minimum of liquid. Exemplary hydraulic properties of the medium that can be measured include the unsaturated hydraulic conductivity of the medium (i.e., the unsaturated liquid flow capability within the medium), the saturated hydraulic conductivity of the medium (i.e., the saturated liquid flow capability within the medium, also known as "K-sat"), rates of liquid permeation/infiltration into the medium (i.e., rates of liquid consumption by the medium), the sorptivity of the medium, and the porosity of the medium, among others.

Additionally and as will be appreciated from the more detailed description that follows, the apparatus embodiments described herein produce liquid consumption and flow rate measurements in non-Mariotte bubbler systems which are free of "bubbling noise" and thus have a high degree of accuracy. The apparatus embodiments can also be deployed in situ quickly, easily and inexpensively. The apparatus embodiments are also both economical and easy to use. The apparatus embodiments are also easy and cost effective to maintain in the event that any individual component thereof requires servicing or replacement. The apparatus embodiments can also be used to model and predict the subsurface contamination characteristics of various liquids and soluble chemicals as they saturate a given porous medium.

1.1 Architectural Framework

FIG. 1 illustrates an exemplary embodiment, in simplified form, of an architectural framework for the apparatus embodiments described herein. As exemplified in FIG. 1, the architectural framework 100 generally includes the following components. A liquid processing subsystem 102 is interfaced 110 with a porous medium 108 whose hydraulic properties are being measured, where this interface is implemented in a manner that establishes liquid contact between the liquid processing subsystem and the medium. The liquid processing subsystem is herein also referred to as a "medium-interfacing means". As will be described in more detail hereafter, the interface between the liquid processing subsystem and the medium can be implemented in various ways depending on the particular application the apparatus embodiments are being used in. More particularly, the implementation of this interface depends on various factors such as the particular type of liquid processing subsystem that is being used, the particular type of medium the liquid processing subsystem is interfacing with, and the particular hydraulic properties that are being measured, among others.

Generally speaking and referring again to FIG. 1, a liquid weighing subsystem 104 is connected to the liquid processing subsystem 102, where this connection can be implemented in various ways which will be described in more detail hereafter. The liquid weighing subsystem is herein also referred to as a "liquid-sourcing means". In the various exemplary implementations of the apparatus embodiments that are described hereafter, the liquid weighing subsystem is remotely located from the liquid processing subsystem, where the distance between the liquid weighing and liquid processing subsystems depends upon various factors such as those which were just described, among others. It is noted however that alternate implementations of the apparatus embodiments are also possible where the liquid weighing and liquid processing subsystems are integrated rather than being remotely located from one another. It is further noted that although the liquid weighing and liquid processing subsystems are illustrated to be level with each other in FIG. 1, this does not imply that they will always be level with each other. As will be appreciated from the more detailed description of the apparatus embodiments that follows, the liquid weighing and liquid processing subsystems can and often will be at different levels with relation to the porous medium 108.

Referring again to FIG. 1, and as will be appreciated from the more detailed description that follows, the architectural framework 100 generally serves to establish liquid conductivity between the liquid weighing subsystem 104 and the porous medium 108. More particularly, the liquid processing subsystem 102 and liquid weighing subsystem are sealably interconnected via an interconnecting liquid tube 106. The interconnecting liquid tube is herein also referred to as a "liquid-transferring means". The liquid processing subsystem and liquid weighing subsystem can optionally also be sealably interconnected via an interconnecting air tube 112. The liquid weighing subsystem stores a liquid (not shown) that flows from the liquid weighing subsystem, through the interconnecting liquid tube, through the liquid processing subsystem, and into the medium until the medium is saturated with the liquid such that the liquid reaches a "steady state of flow". It is noted that, depending on the saturation characteristics of the medium at a given point in time, the liquid can flow from the liquid weighing subsystem, through the interconnecting liquid tube and liquid processing subsystem, and into the medium.

Referring again to FIG. 1, the liquid weighing subsystem 104 either automatically or manually monitors the weight of the liquid stored therein. In other words, the liquid weighing subsystem either automatically or manually measures the weight of the liquid stored therein on an ongoing basis. As such, the liquid weighing subsystem measures the amount of liquid that flows between the liquid weighing subsystem and the porous medium 108. The liquid weighing subsystem uses the liquid weight measurements to determine one or more hydraulic properties of the medium. By way of example but not limitation, the liquid weighing subsystem can use the liquid weight measurements to determine the direction of the liquid flow (i.e., whether the liquid is flowing into or out of the medium) at any given point in time. The liquid weighing subsystem can also use the liquid weight measurements to determine the rate of the liquid flow (i.e. the rate at which the medium consumes the liquid) at any given point in time.

1.2 Liquid Weighing Subsystem

Figure 2:
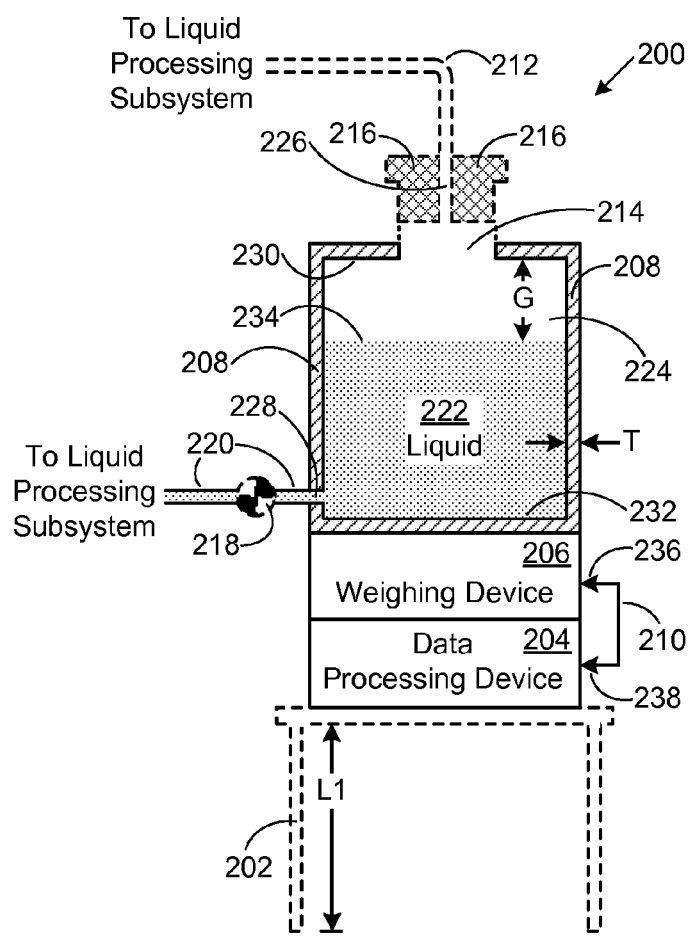
FIG. 2 is a diagram illustrating a front elevational view, in simplified form and partly in cross-section, of an exemplary embodiment of a liquid weighing subsystem of the apparatus embodiments described herein.

FIG. 2 illustrates a front elevational view, in simplified form and partly in cross-section, of an exemplary embodiment of the liquid weighing subsystem. As exemplified in FIG. 2, the liquid weighing subsystem 200 generally includes a reservoir 208, a weighing device 206, and a data processing device 204. The reservoir has a hollow interior 224 which is partially filled with a liquid 222 when the liquid weighing subsystem is in operational use. In other words, the interior of the reservoir is substantially but not completely filled with the liquid such that an air gap G exists between the top interior surface 230 of the reservoir and the top surface 234 of the liquid therein. In an exemplary embodiment of the apparatus described herein the liquid is water. However, alternate embodiments of the apparatus are also possible where the liquid can be any of the other aforementioned types of liquids.

Referring again to FIG. 2, the reservoir 208 is centrally disposed on top of the weighing device 206, thus enabling the weighing device to either automatically or manually measure the weight of the liquid 222 in the reservoir on an ongoing basis. The weighing device includes a first data port 236. The data processing device 204 includes a second data port 238. The first and second data ports are interconnected via a data connection 210. In the apparatus embodiments described herein both the first and second data ports are a conventional Universal Serial Bus (USB) port and the data connection is accordingly a conventional USB connection. It is noted that alternate apparatus embodiments are also possible which employ other types of data ports and related data connections. By way of example but not limitation, both the first and second data ports can be a conventional wireless networking port and the data connection can accordingly be a conventional wireless networking connection.

Referring again to FIG. 2, the weighing device 206 continuously measures the weight of the liquid 222 in the reservoir 208. The data processing device 204 uses the data connection 210 to routinely read the weight measurements made by the weighing device at a prescribed interval of time over a prescribed duration of time after the porous medium has become saturated with the liquid such that the liquid reaches a steady state of flow. The data processing device also stores each of the read weight measurements in a time and date stamped format. In other words, the data processing device continuously monitors the weight of the liquid within the reservoir. Generally speaking, the prescribed interval and duration of time that are used depend on the type of medium that is being tested and its permeability. With regard to the prescribed interval of time, a shorter interval will generally be used for a medium having a higher permeability, and a longer interval will generally be used for a medium having a lower permeability. In an exemplary implementation of the apparatus embodiments described herein, the prescribed interval of time is approximately 60 seconds for a sand-based soil and 5 minutes for a dense, clay-based soil. In this same exemplary implementation, the prescribed duration of time is approximately 10 minutes for the sand-based soil and 30 minutes for the dense, clay-based soil.

Referring again to FIG. 2, the data processing device 204 can also analyze the stored weight measurements in a prescribed manner in order to compute changes in the amount of the liquid 222 (e.g., increases or decreases in the liquid level) in the reservoir 208 over time, and from these changes compute one or more desired hydraulic properties of the porous medium which is being tested. The data processing device can also convert the measured liquid weights to a liquid volume. The liquid weighing subsystem can optionally also include an elevating device 202. The reservoir, weighing device, data processing device, and elevating device will now be described in more detail.

Referring again to FIG. 2, the reservoir 208 can have various exterior shapes, exterior sizes, interior 224 liquid volumes, and wall thicknesses T, each of which are generally application dependent. In an exemplary embodiment of the apparatus described herein the reservoir has an exterior horizontally cross-sectional shape which is substantially rectangular, an exterior size of approximately 10 inches long×7 inches wide×9 inches high, an interior liquid volume of approximately 8 liters, and wall thickness T of approximately 0.035 of an inch. The reservoir can be constructed from any material which is substantially rigid, inert and impervious to the liquid 222 which is being held there-within, where this material can be either transparent or non-transparent. By way of example but not limitation, the reservoir can be constructed from either plastic, or glass, or a non-porous ceramic.

Referring again to FIG. 2, an opening 214 exists on the top of the reservoir 208. An optional removable reservoir cap 216 can be sealably fitted into the opening. For the apparatus embodiments described hereafter which employ the reservoir cap, when these embodiments are initially placed into operational use in situ, the reservoir cap is removed from the opening to allow the liquid 222 to be added through the opening in order to partially fill the hollow interior 224 of the reservoir with the liquid. Once the interior of the reservoir has been partially filled with the liquid, the reservoir cap is sealably re-fitted into the opening. Whenever the liquid level in the reservoir gets low, the reservoir cap can be briefly removed from the opening and the liquid can be added through the opening in order to partially refill the interior of the reservoir with the liquid. Once the interior of the reservoir has been partially refilled with the liquid, the reservoir cap can be sealably re-fitted into the opening.

Referring again to FIG. 2, the removable reservoir cap 216 can be constructed from any material which is relatively stiff, inert, impervious to the liquid 222, and is capable of being repeatedly sealably fitted into and removed from the opening 214 on the top of the reservoir 208. By way of example but not limitation, the reservoir cap can be constructed from a substantially hard rubber. The substantially rigid nature of the reservoir material allows the hollow interior 224 of the reservoir to be pressurized to either a low pressure or a partial/moderate vacuum when the reservoir cap is fitted into the reservoir's opening. In other words, in an exemplary embodiment of the apparatus the interior of the reservoir can support a pressure ranging from approximately −1 bar to +1 bar. A reservoir cap passageway 226 exists between the top and bottom of the reservoir cap. A liquid weighing end of an optional interconnecting air tube 212 can be sealably connected to the reservoir cap passageway. For the apparatus embodiments described hereafter which employ the reservoir cap and interconnecting air tube, a liquid processing end of the interconnecting air tube is sealably connected to the liquid processing subsystem (not shown) as will be described in more detail hereafter. The interconnecting air tube can optionally include an air valve (not shown) which generally operates to control the flow of air in the interconnecting air tube. More particularly, whenever the reservoir cap is sealably fitted into the opening on the top of the reservoir and the air valve is open, air can freely flow between the interior of the reservoir and the liquid processing subsystem through the interconnecting air tube and reservoir cap passageway. Whenever the reservoir cap is sealably fitted into the opening on the top of the reservoir and the air valve is closed, no air can flow between the interior of the reservoir and the liquid processing subsystem (i.e., the closure of the air valve effectively serves to sealably close the reservoir cap passageway.

Referring again to FIG. 2, a reservoir passageway 228 exists between the hollow interior 224 and exterior of the reservoir 208. Generally speaking, the reservoir passageway is located on the bottom portion of the reservoir. More particularly, in the reservoir embodiment exemplified in FIG. 2 the reservoir passageway is located on a side wall of the reservoir near the bottom surface 232 of the interior of the reservoir. A liquid weighing end of an interconnecting liquid tube 220 is sealably connected to the reservoir passageway. A liquid processing end of the interconnecting liquid tube is sealably connected to the liquid processing subsystem as will be described in more detail hereafter.

Referring again to FIG. 2, the interconnecting liquid tube 220 can optionally include a liquid valve 218 which generally operates to control the flow of the liquid 222 in the interconnecting liquid tube. More particularly, whenever the liquid is present in the hollow interior 224 of the reservoir 208 and the liquid valve is open, the liquid can freely flow between the interior of the reservoir and the liquid processing subsystem through the interconnecting liquid tube and reservoir passageway 228. Whenever the liquid is present in the interior of the reservoir and the liquid valve is closed, no liquid can flow between the interior of the reservoir and the liquid processing subsystem (i.e., the closure of the liquid valve effectively serves to sealably close the reservoir passageway). It will thus be appreciated that the liquid valve is advantageous since it allows the liquid to be added to the reservoir before the liquid processing end of the interconnecting liquid tube is sealably connected to the liquid processing subsystem.

Referring again to FIG. 2, it will be appreciated that various types and diameters of conventional vacuum tubing can be used for the interconnecting air tube 212 and interconnecting liquid tube 220. The interior diameter of the interconnecting air tube and liquid tube are sized such that a tight seal is established with the reservoir cap passageway 226 and reservoir passageway 228 respectively. By way of example but not limitation, in the apparatus embodiments described herein the interconnecting air tube and liquid tube can have an interior diameter in the range of approximately ⅛ of an inch to ¼ of an inch.

Referring again to FIG. 2, the weighing device 206 includes a weighing platform (not shown) that is generally sized to fit the bottom of the reservoir 208. The weighing device has a maximum weight capacity which is generally dependent on the interior liquid volume of the reservoir. In the aforementioned exemplary apparatus embodiment where the reservoir has an interior liquid volume of approximately 8 liters, the weighing device can have a maximum weight capacity in the range of approximately 5 kilograms to 20 kilograms. The weighing device can optionally be weather resistant, which is advantageous since the liquid weighing subsystem 200 operates in situ and thus can be exposed to various types of weather. It will thus be appreciated that the weather resistance feature of the weighing device serves to increase the operating life of the weighing device. The weighing device can produce weight measurements in either metric units or imperial units.

Referring again to FIG. 2, various types of scales can be used for the weighing device 206. By way of example but not limitation, in the apparatus embodiments described herein the weighing device is a conventional digital scale having the following additional features and functionality. The digital scale has a maximum weight capacity of approximately 10 kilograms. The digital scale also has a moderate measurement precision (e.g., a measurement precision of approximately 0.2 grams or better). The digital scale can be powered in various ways such as an external AC (alternating current) source, or an internal battery source (which is advantageous based on the in situ operation of the scale), among others. The digital scale can optionally include a visual display (such as a backlit liquid crystal display (LCD), or the like) for displaying the current weight measurement and other types of information.

Referring again to FIG. 2, the liquid weighing subsystem 200 can optionally be temperature compensated in various ways, examples of which will now be described in more detail. Such temperature compensation is advantageous since the liquid weighing subsystem can be exposed to a wide range of different temperatures and the temperature compensation serves to further increase the accuracy of the liquid 222 measurements made by the liquid weighing subsystem when it is exposed to variations in temperature. In the case where the weighing device 206 is a digital scale, the electronic circuitry within the scale can be temperature compensated. In the case where the data processing device 204 is converting the measured liquid weights to a liquid volume, the data processing device can adjust its computed results for liquid temperature. A temperature sensing device can also be installed inside the reservoir 208 and connected to the data processing device, thus allowing the data processing device to read the current temperature of the liquid and adjust its computed results accordingly.

Referring again to FIG. 2, the data processing device 204 has the following additional features and functionality. The data processing device includes digital clock functionality which can be used to time and date stamp each of the weight measurements it reads from the weighing device 206. The data processing device can optionally also include another data port (not shown) to which a removable data storage device (not shown) can be connected. In the apparatus embodiments described herein this other data port is also a USB port and the removable data storage device is a conventional USB flash drive having a capacity of 2 gigabytes or greater. The data processing device can both read information from and write information to the removable data storage device. Accordingly, the removable data storage device can be used to download information (such as software programs, configuration settings, and the like) to the data processing device, thus making the data processing device field programmable. The removable data storage device can also be used to transfer information (such as the weight measurements and related hydraulic properties which are computed therefrom) from the data processing device to another computing device for further analysis.

Referring again to FIG. 2, the data processing device 204 can optionally also include Global Positioning System (GPS) functionality which can be used to identify the specific geographic location where the hydraulic properties are being measured. The data processing device can optionally also include alarm functionality which can be used to audibly and/or visually inform a user of a prescribed condition (such as when the apparatus embodiments described herein reach a prescribed steady-state liquid flow rate condition, among others). The data processing device can be powered in various ways such as an external AC source, or an internal battery source (which is advantageous based on the in situ operation of the device), among others. The data processing device can optionally also include a visual display (such as a backlit LCD, or the like) for displaying the hydraulic properties that are computed by the device, along with other types of information, to a user. The data processing device can be implemented in various ways. By way of example but not limitation, in one embodiment of the apparatus described herein the data processing device can be a custom designed computing device that is packaged in a weather resistant enclosure, which is advantageous for the same reasons given above. In another embodiment of the apparatus the data processing device can be either a conventional laptop computer or tablet computer, among other things.

Referring again to FIG. 2, the data processing device 204 can be physically configured within the liquid weighing subsystem 200 in various ways including, but not limited to, the following. In one embodiment of the apparatus described herein where the data processing device is implemented in a sturdy enclosure which is capable of bearing the combined weight of the weighing device 206, the reservoir 208 and the liquid 222 therein, the weighing device and reservoir can be disposed on top of the data processing device as exemplified in FIG. 2. In another embodiment of the apparatus (not shown) where the data processing device is either a conventional laptop computer or tablet computer, the weighing device and reservoir would not be disposed on top of the data processing device, but rather the data processing device would be located nearby the weighing device.

Referring again to FIG. 2, the optional elevating device 202 can serve various purposes including, but not limited to, the following. The elevating device can be used to provide a sturdy/stable and level platform for the weighing device 206, reservoir 208 and data processing device 204. It will be appreciated that having the weighing device and reservoir rest atop a sturdy/stable and level platform is advantageous since it serves to optimize the accuracy of the weight measurements being made by the weighing device. The elevating device has three or more legs which are individually user-adjustable to a desired length L1. In an exemplary embodiment of the apparatus described herein the elevating device is an adjustable height table having legs that can be individually adjusted by a user to a length L1 that is between approximately 13 inches and 29 inches. The elevating device can optionally also be used to elevate the reservoir in order to create a prescribed amount of overhead pressure in the apparatus embodiments described herein. As will be described in more detail hereafter, this overhead pressure can be used to adjust the liquid head height in the apparatus embodiments. The elevating device is generally easy to assemble, adjust and disassemble, which is advantageous based on the in situ nature of the apparatus embodiments.

1.3 Automated Constant Head Borehole Permeameter

Figure 3:
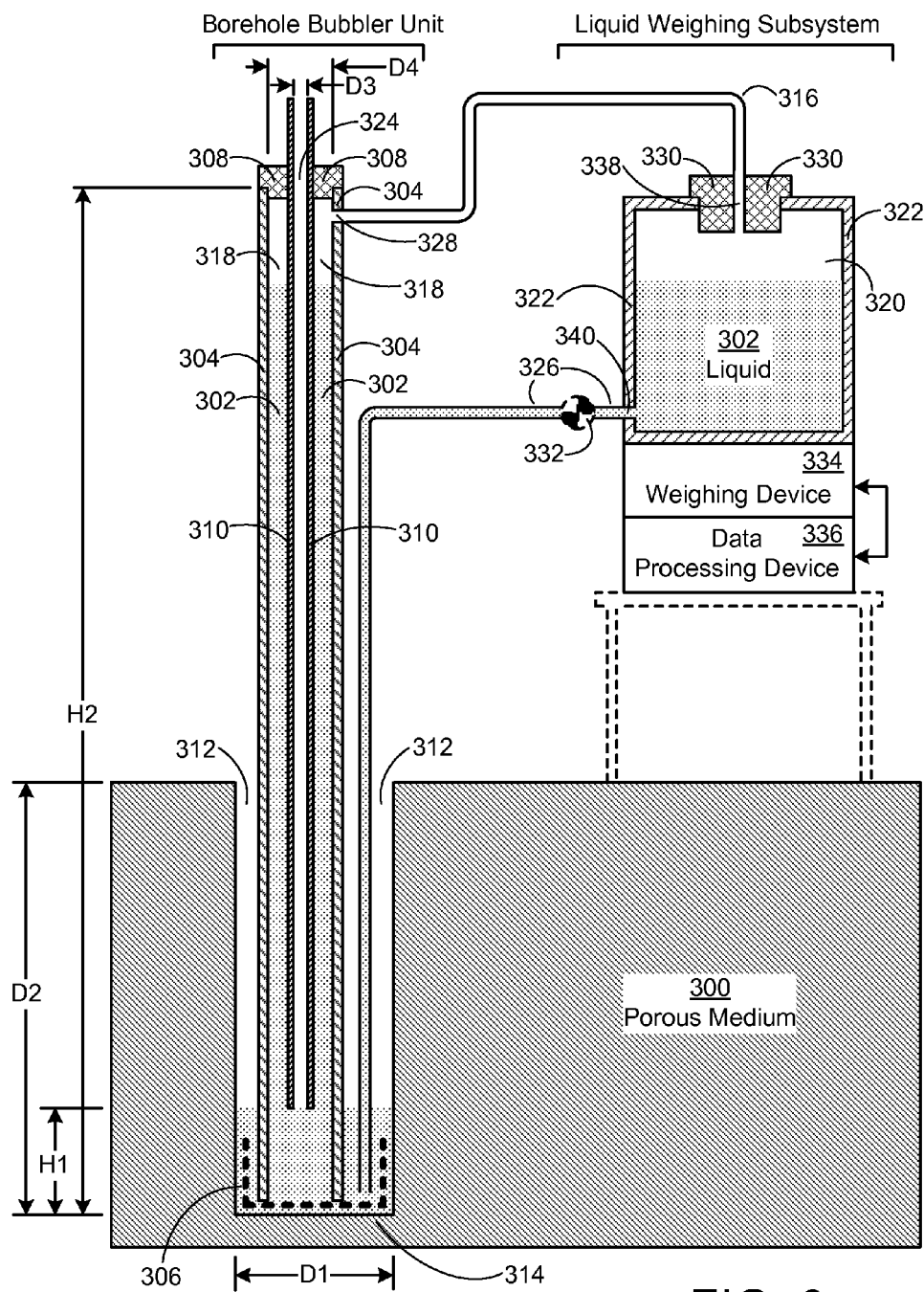
FIG. 3 is a diagram illustrating a front elevational view, in simplified form and partly in cross-section, of one exemplary automated constant head borehole permeameter implementation of the apparatus embodiments described herein.

FIG. 3 illustrates a front elevational view, in simplified form and partly in cross-section, of one exemplary automated constant head borehole permeameter implementation of the apparatus embodiments described herein (hereafter simply referred to as a "first permeameter embodiment"). The first permeameter embodiment exemplified in FIG. 3 can be used to measure various hydraulic properties of the porous medium 300 such as the saturated hydraulic conductivity of the medium, among others. In the first permeameter embodiment described in this section the liquid weighing subsystem is implemented in the manner described heretofore. The liquid processing subsystem is a modified version of a conventional Mariotte bubbler (also known as a Mariotte column or Mariotte siphon, among other names) which is hereafter simply referred to as a "borehole bubbler unit." As is exemplified in FIG. 3 and will be described in more detail hereafter, the borehole bubbler unit includes an elongated liquid tube 304, a dispersive end cap 306, a tube cap 308, and an elongated air tube 310 which is slidably user-adjustable within the interior of the elongated liquid tube. The bubbler unit is inserted into a borehole 312 that is formed in the porous medium such that the dispersive end cap abuts the bottom 314 of the borehole, and the bottom end of the elongated air tube is a prescribed distance H1 from the bottom of the borehole. The first permeameter embodiment is advantageous in that it makes it possible to study the combination of both gravity and capillary forces on the saturated hydraulic conductivity of the medium.

Referring again to FIG. 3, the elongated liquid tube 304 of the borehole bubbler unit has a prescribed height H2, a prescribed radially cross-sectional shape, and a prescribed interior diameter D4. The elongated air tube 310 of the bubbler unit has a prescribed interior diameter D3 and a prescribed height which is large enough to allow the elongated air tube to be slidably adjusted by a user to a downward-most position in which the bottom end of the elongated air tube abuts the top surface of the dispersive end cap 306 while the top end of the elongated air tube still extends above the top of the tube cap 308. It will be appreciated that the elongated liquid tube can have various heights H2, various radially cross-sectional shapes, and various interior diameters D4, and the elongated air tube can have various interior diameters D3. In an exemplary embodiment of the first permeameter described in this section the elongated liquid tube has a height H2 of approximately 7 feet, a radially cross-sectional shape which is substantially circular, and an interior diameter D4 of approximately ¾ of an inch, and the elongated air tube has an interior diameter D3 of approximately ⅛ of an inch. It will also be appreciated that the borehole 312 can have various depths D2 and any diameter D1 that is large enough to allow the bubbler unit to be inserted therein. The particular diameter D1 and depth D2 of the borehole that are used are generally application dependent and are selected based on the dimensions of the bubbler unit, the type of porous medium 300 that is being tested, and the particular hydraulic properties of the medium that are being measured, among other things. In the just mentioned exemplary embodiment of the first permeameter the borehole has a diameter D1 of approximately 4 inches and a depth D2 of up to approximately 4 feet.

Referring again to FIG. 3, the bottom end of the elongated liquid tube 304 abuts the top surface of the dispersive end cap 306. The end cap is perforated in order to allow the liquid 302 to flow there-through. The end cap serves to reduce the kinetic energy of the liquid as it flows out of the borehole bubbler unit and into the borehole 312 and vice versa, and thus serves to minimize erosion of the borehole. The tube cap 308 is sealably fitted onto the top end of the elongated liquid tube. A tube cap passageway 324 exists between the top and bottom of the tube cap. The elongated air tube 310 is sealably but slidably inserted into the tube cap passageway such that the bottom end of the elongated air tube extends a prescribed distance into the interior of the elongated liquid tube and the top end of the elongated air tube extends above the top of the tube cap, where this distance can be adjusted by a user sliding the elongated air tube up or down through the tube cap passageway. The top end of the elongated air tube is open to the in situ ambient air.

Generally speaking and referring again to FIG. 3, the aforementioned liquid weighing subsystem is sealably connected to the borehole bubbler unit via both an interconnecting air tube 316 and an interconnecting liquid tube 326. More particularly, after the hollow interior 320 of the reservoir 322 has been partially filled with the liquid 302 as described heretofore, the removable reservoir cap 330 is sealably fitted into the opening on the top of the reservoir and the liquid weighing end of the interconnecting air tube is sealably connected to the reservoir cap passageway 338 between the top and bottom of the reservoir cap. A tube passageway 328 exists between the interior 318 and exterior of the elongated liquid tube 304, where this passageway is located on a side wall of the elongated liquid tube near the top end thereof. The liquid processing end of the interconnecting air tube is sealably connected to the tube passageway, thus allowing air to flow between the interior of the elongated liquid tube and the interior 320 of the reservoir through the interconnecting air tube. The liquid processing end of the interconnecting liquid tube is inserted into the borehole 312 next to the elongated liquid tube such that this end either abuts or is substantially near the top surface of the dispersive end cap 306.

Referring again to FIG. 3, the elongated liquid tube 304 and elongated air tube 310 can be constructed from any material which is substantially rigid, inert and impervious to the liquid 302, where this material can be either transparent or non-transparent. By way of example but not limitation, the elongated liquid tube and elongated air tube can be constructed from either plastic, or glass, or metal. The dispersive end cap 306 can be constructed from any material which is inert to the liquid while being porous at the same time, such as woven plastic, or glass, or metal, or porous ceramic. The tube cap 308 can be constructed from any material which is relatively stiff, inert, impervious to the liquid, and is capable of being sealably fitted onto the top end of the elongated liquid tube and allowing the elongated air tube to be sealably moved up and down in the tube cap passageway 324. By way of example but not limitation, the tube cap can be constructed from a hard rubber, or plastic, or metal.

Referring again to FIG. 3, the first permeameter embodiment described in this section generally operates in the following manner. After the hollow interior 320 of the reservoir 322 has been partially filled with the liquid 302, and the liquid valve 332 on the interconnecting liquid tube 326 has been opened (assuming this liquid tube includes this optional liquid valve), and the optional air valve (not shown) on the interconnecting air tube 316 has also been opened (assuming this air tube includes this air valve), the liquid will flow from the interior of the reservoir, through the reservoir passageway 340, through the interconnecting liquid tube, and into the borehole 312 until a constant liquid head is established at the bottom of the borehole. As is exemplified in FIG. 3, this head has a height which is equal to the distance H1 between the bottom end of the elongated air tube 310 and the bottom 314 of the borehole. In an exemplary embodiment of the first permeameter the distance H1 is approximately 4 inches. It will be appreciated that the height of the constant liquid head can be increased by a user sliding the elongated air tube up through the tube cap passageway 324, and can be decreased by the user sliding the elongated air tube down through the tube cap passageway.

Referring again to FIG. 3, it will be appreciated that as the liquid 302 flows into the borehole 312 a partial vacuum (i.e., a negative pressure) is established in the hollow interior 320 of the reservoir 322 which causes the liquid to rise up into the interior 318 of the elongated liquid tube 304 until the height of the liquid within this tube is approximately the same as the height of the liquid within the reservoir. The first permeameter embodiment described in this section serves to maintain the height of the liquid head in the borehole at the distance H1. In other words, as the liquid within the borehole permeates into the porous medium 300 additional liquid will flow from the interior of the reservoir, through the interconnecting liquid tube 326, and into the bottom of the borehole in order to maintain the height of the liquid head therein at the distance H1. As described heretofore, the weighing device 334 continuously measures the weight of the liquid within the reservoir, and the data processing device 336 routinely reads and stores the weight measurements. The data processing device can analyze the stored weight measurements on an ongoing basis to determine when a prescribed steady-state liquid flow rate condition has been reached. Once this condition has been reached, the data processing device can further analyze the stored weight measurements to compute the saturated hydraulic conductivity of the medium, among other things.

Figure 4:
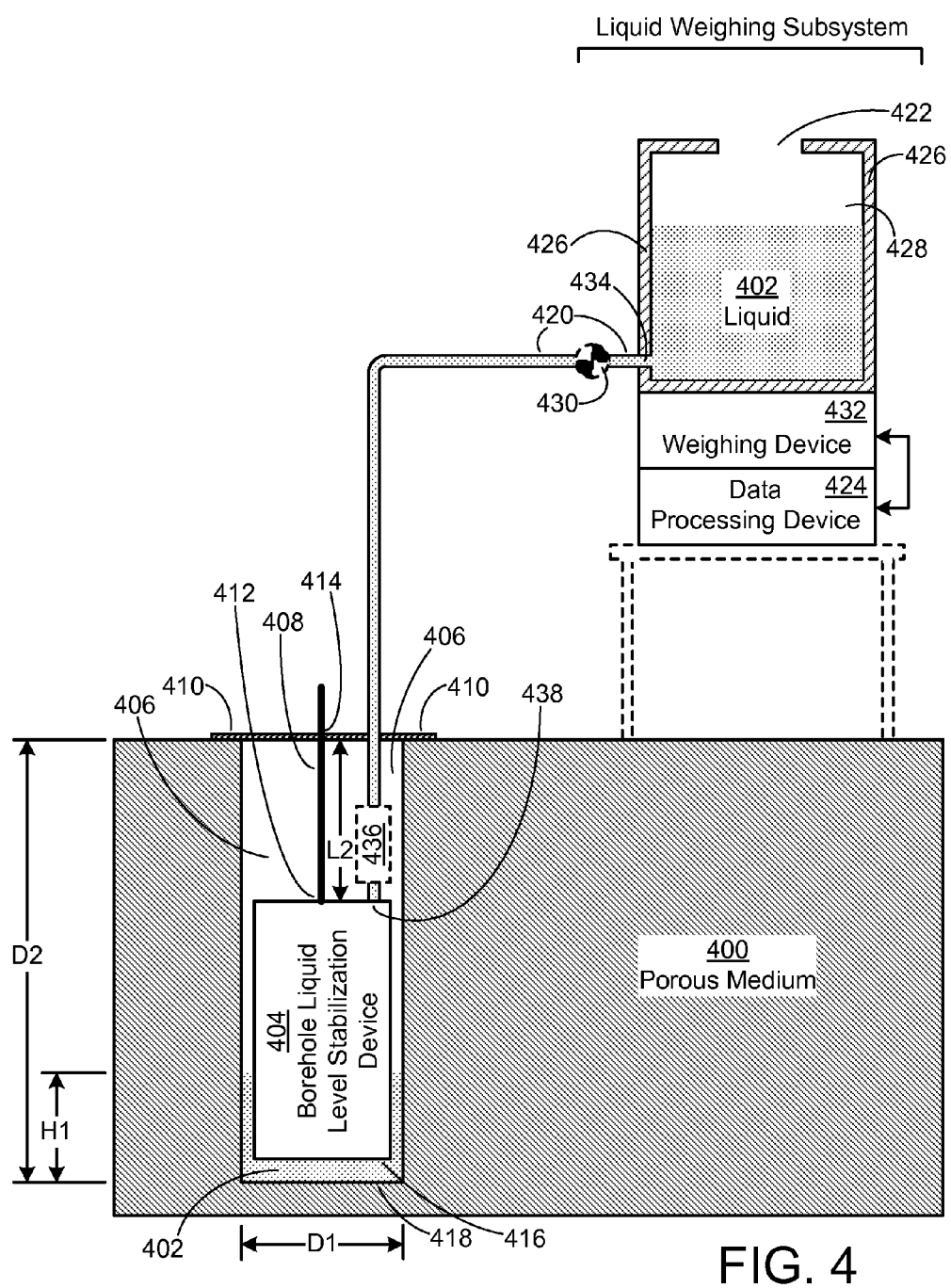
FIG. 4 is a diagram illustrating a front elevational view, in simplified form and partly in cross-section, of another exemplary automated constant head borehole permeameter implementation of the apparatus embodiments described herein.

FIG. 4 illustrates a front elevational view, in simplified form and partly in cross-section, of another exemplary automated constant head borehole permeameter implementation of the apparatus embodiments described herein (hereafter simply referred to as the "second permeameter embodiment"). The second permeameter embodiment exemplified in FIG. 4 can be used to measure various hydraulic properties of the porous medium 400 such as the saturated hydraulic conductivity of the medium, among others. In the second permeameter embodiment described in this section the liquid weighing subsystem is implemented in the manner described heretofore. The liquid processing subsystem is a conventional float valve type borehole liquid level stabilization device 404 which is hereafter simply referred to as a "liquid level stabilization device". It is noted that alternate implementations of the second permeameter embodiment (not shown) are also possible where the liquid processing subsystem can be other types of devices such as a conventional solenoid valve type borehole liquid level stabilization device.

As exemplified in FIG. 4, the liquid level stabilization device 404 is adjustably suspended at a prescribed depth within a borehole 406 that is formed in the porous medium 400, where this adjustable suspension is implemented in a manner that allows this depth to be adjusted by a user. It will be appreciated that this suspension can be implemented in various ways. By way of example but not limitation, in the second permeameter embodiment exemplified in FIG. 4, a cable 408 and a cable retention member 410 are used to adjustably suspend the liquid level stabilization device in the borehole as follows. The bottom end of the cable is fastened 412 to the liquid level stabilization device. The retention member is disposed on the top surface of the medium (e.g., the member can diametrically extend across the top of the borehole as exemplified in FIG. 4). A prescribed point 414 on the upper portion of the cable is adjustably fastened to the retention member. The cable is long enough to allow the bottom 416 of the liquid level stabilization device to abut the bottom 418 of the borehole. The depth of the liquid level stabilization device within the borehole can be adjusted by the user changing the length L2 of cable that exists between the retention member and the device (i.e., changing the point 414 on the upper portion of the cable that is fastened to the retention member). The second permeameter embodiment described in this section is advantageous in that it makes it possible to study the combination of both gravity and capillary forces on the saturated hydraulic conductivity of the medium.

Referring again to FIG. 4, it will be appreciated that the borehole 406 can have various depths D2 and any diameter D1 that is large enough to allow the liquid level stabilization device 404 to be suspended therein. The particular diameter D1 and depth D2 of the borehole that are used are generally application dependent and are selected based on the dimensions of the liquid level stabilization device, the type of porous medium 400 that is being tested, and the particular hydraulic properties of the medium that are being measured, among other things. In an exemplary embodiment of the second permeameter described in this section the liquid level stabilization device has an outer diameter of approximately 3 inches and an outer height of approximately 14 inches, and the borehole has a diameter D1 of approximately 4 inches and a depth D2 of up to 10 feet.

Generally speaking and referring again to FIG. 4, the aforementioned liquid weighing subsystem is sealably connected to the liquid level stabilization device 404 via just an interconnecting liquid tube 420. More particularly and as exemplified in FIG.FIG. 4, the opening 422 on the top of the reservoir 426 is open to the in situ ambient air. The liquid processing end of the interconnecting liquid tube is sealably connected to the liquid level stabilization device. In the second permeameter embodiment exemplified in FIG. 4, this connection 438 is made on the top of the liquid level stabilization device. It is noted however that an alternate embodiment of the second permeameter is also possible where this connection is made on the side of the liquid level stabilization device. The second permeameter embodiment described in this section generally operates in the following manner. After the hollow interior 428 of the reservoir has been partially filled with the liquid 402 and the liquid valve 430 on the interconnecting liquid tube 420 has been opened (assuming this tube includes this optional valve), the liquid will flow from the interior of the reservoir, through the reservoir passageway 434, through the interconnecting liquid tube, through the liquid level stabilization device, and into the borehole 406 until a constant liquid head having a prescribed height H1 is established at the bottom 418 of the borehole.

Referring again to FIG. 4, the height H1 of the constant liquid head is based on the depth at which the liquid level stabilization device 404 is adjustably suspended within the borehole 406. The height H1 of the constant liquid head can be increased by decreasing the depth at which the liquid level stabilization device is adjustably suspended within the borehole (e.g., decreasing the length L2 of cable 408 that exists between the cable retention member 410 and the device). The height H1 of the constant liquid head can be decreased by increasing the depth at which the liquid level stabilization device is adjustably suspended within the borehole (e.g., increasing the length L2 of the cable). The cable can be marked with distance measurement indicators that allow a user to conveniently visually determine the depth D2 of the borehole and the current height H1 of the constant liquid head. In an exemplary embodiment of the second permeameter described in this section the height H1 of the constant liquid head is approximately 3 inches when the bottom 416 of the liquid level stabilization device abuts the bottom 418 of the borehole.

Referring again to FIG. 4, the interior of the liquid level stabilization device 404 includes a floating valve (not shown) which serves to control the flow rate of the liquid 402 into the borehole 406 in order to maintain the liquid head therein at the height H1. In other words, as the liquid within the borehole permeates into the porous medium 400 the liquid level stabilization device will allow additional liquid to flow from the hollow interior 428 of the reservoir 426, through the interconnecting liquid tube 420, and into the bottom of the borehole in order to maintain the liquid head therein at the height H1. As described heretofore, the weighing device 432 continuously measures the weight of the liquid within the reservoir, and the data processing device 424 routinely reads and stores the weight measurements. The data processing device can analyze the stored weight measurements on an ongoing basis to determine when a prescribed steady-state liquid flow rate condition has been reached. Once this condition has been reached, the data processing device can further analyze the stored weight measurements to compute the saturated hydraulic conductivity of the medium, among other things.

Referring again to FIG. 4, in an alternate embodiment of the second permeameter the liquid weighing subsystem can optionally include a pressure regulator unit 436 which is installed along the interconnecting liquid tube 420 very near the liquid processing end thereof (i.e., the pressure regulator unit is connected inline with the interconnecting liquid tube and is located as close as possible to the liquid level stabilization device 404). The pressure regulator unit serves to control the liquid overhead pressure to the liquid level stabilization device. The pressure regulator unit is employed when the liquid level stabilization device is suspended within a deep borehole 406 (e.g., a borehole whose depth D2 is greater than 10 feet). The use of the pressure regulator unit allows the liquid level stabilization device to be suspended within a borehole having a depth D2 of up to 50 feet.

1.4 Automated Constant Head Double-Ring Infiltrometer

Figure 5:
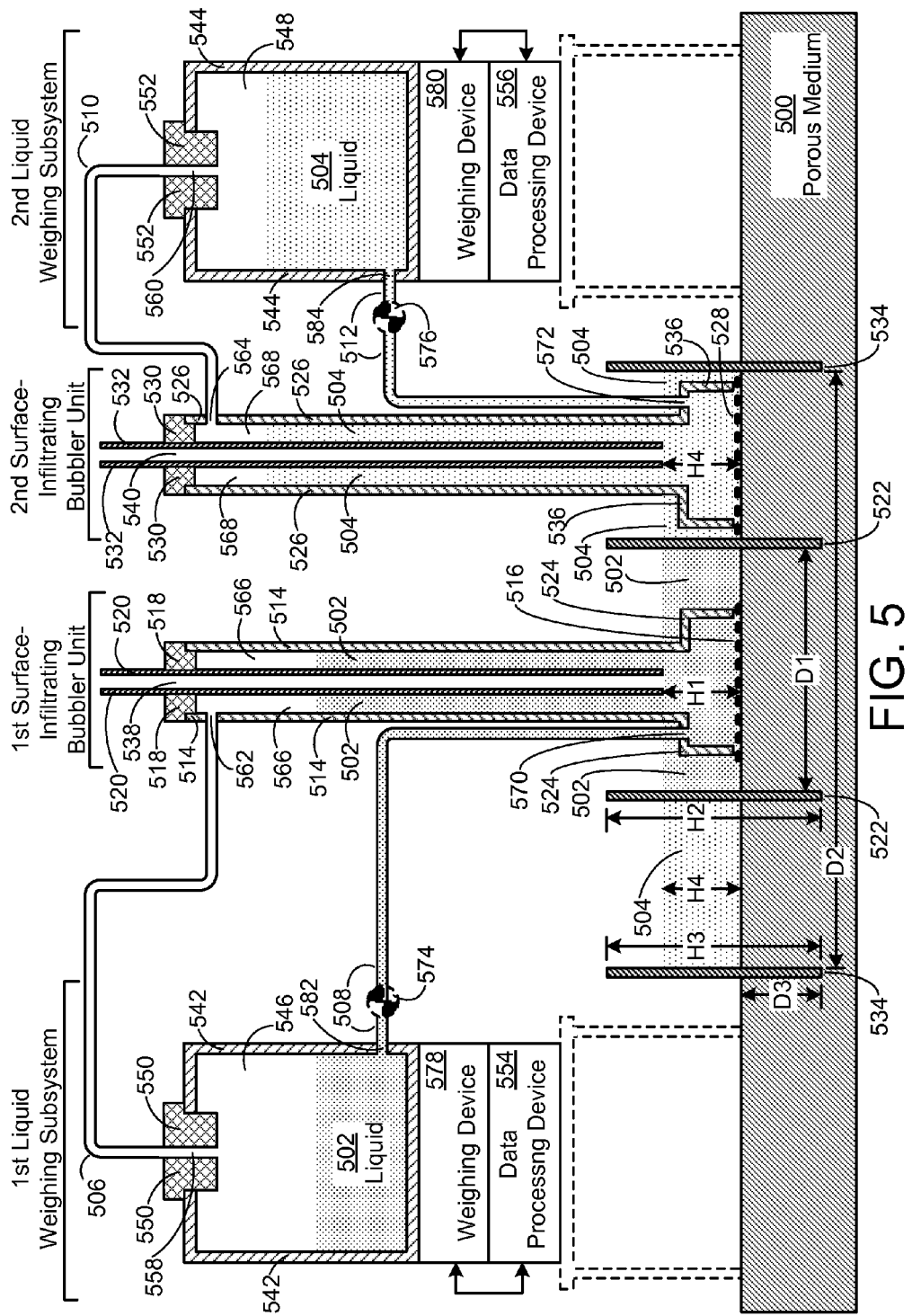
FIG. 5 is a diagram illustrating a front elevational view, in simplified form and partly in cross-section, of an exemplary automated constant head double-ring infiltrometer implementation of the apparatus embodiments described herein.

FIG. 5 illustrates a front elevational view, in simplified form and partly in cross-section, of an exemplary automated constant head double-ring infiltrometer implementation of the apparatus embodiments described herein (hereafter simply referred to as the "double-ring infiltrometer embodiment"). The double-ring infiltrometer embodiment exemplified in FIG. 5 can be used to measure various hydraulic properties of the porous medium 500 such as the saturated hydraulic conductivity of the medium, among others. As is exemplified in FIG. 5 and will be described in more detail hereafter, the double-ring infiltrometer embodiment described in this section includes two separate liquid weighing subsystems and two separate liquid processing subsystems. Each of the liquid weighing subsystems is implemented in the manner described heretofore. Each of the liquid processing subsystems is a modified version of a conventional Mariotte bubbler. As such, the first liquid processing subsystem is hereafter simply referred to as a "first surface-infiltrating bubbler unit" and the second liquid processing subsystem is hereafter simply referred to as a "second surface-infiltrating bubbler unit." The first liquid weighing subsystem is sealably connected to the first surface-infiltrating bubbler unit via both a first interconnecting air tube 506 and a first interconnecting liquid tube 508. The second liquid weighing subsystem is sealably connected to the second surface-infiltrating bubbler unit via both a second interconnecting air tube 510 and a second interconnecting liquid tube 512.

The double-ring infiltrometer embodiment makes it possible to study the force of gravity on the saturated hydraulic conductivity of the medium.

Referring again to FIG. 5, the first surface-infiltrating bubbler unit includes a first elongated liquid tube 514, a first dispersive end cap 516, a first tube cap 518, and a first elongated air tube 520 which is slidably user-adjustable within the interior of the first elongated liquid tube. As exemplified in FIG. 5, an inner infiltration ring 522 has a prescribed interior diameter D1 and a prescribed height H2. The bottom end of the inner infiltration ring is axially embedded into the porous medium 500 a prescribed depth D3, where the depth D3 is less than the height H2 such that the top end of the inner infiltration ring axially extends above the top surface of the medium. Although the term "ring" is used to refer to the inner infiltration ring, it is noted that the inner infiltration ring can have a variety of radial cross-sectional shapes. In an exemplary embodiment of the double-ring infiltrometer described in this section, the inner infiltration ring has a substantially circular radial cross-sectional shape. Alternate embodiments of the double-ring infiltrometer are also possible where the inner infiltration ring has a radial cross-sectional shape which is either substantially square, or substantially hexagonal, among other shapes.

Referring again to FIG. 5, the first surface-infiltrating bubbler unit is disposed on the top surface of the porous medium 500 within the interior of the inner infiltration ring 522 such that the first dispersive end cap 516 abuts the top surface of the medium and the bottom end of the first elongated air tube 520 is a prescribed distance H1 from the top surface of the medium. Generally speaking, the bottom end of the first elongated liquid tube 514 abuts the top surface of the first dispersive end cap. In the double-ring infiltrometer embodiment exemplified in FIG. 5, the bottom portion of the first elongated liquid tube tapers radially outward to form a first support base 524 for the first surface-infiltrating bubbler unit, and the bottom end of the first support base abuts the top surface of the first dispersive end cap. Having the first support base is advantageous since it serves to maintain the first surface-infiltrating bubbler unit in a substantially vertical position. It will be appreciated that an alternate embodiment of the double-ring infiltrometer (not shown) is also possible where the bottom portion of the first elongated liquid tube does not taper radially outward (i.e., there is no first support base on the first elongated liquid tube).

Referring again to FIG. 5, the first dispersive end cap 516 is perforated in order to allow the first liquid 502 to flow there-through. The first dispersive end cap serves to reduce the kinetic energy of the first liquid as it flows out of the first surface-infiltrating bubbler unit and into the interior of the inner infiltration ring 522 and vice versa, and thus serves to minimize erosion of the porous medium 500. The first tube cap 518 is sealably fitted onto the top end of the first elongated liquid tube 514. A first tube cap passageway 538 exists between the top and bottom of the first tube cap. The first elongated air tube 520 is sealably but slidably inserted into the first tube cap passageway such that the bottom end of the first elongated air tube extends a prescribed distance into the interior of the first elongated liquid tube and the top end of the first elongated air tube extends above the top of the first tube cap, where this distance can be adjusted by a user sliding the first elongated air tube up or down through the first tube cap passageway. The top end of the first elongated air tube is open to the in situ ambient air.

Referring again to FIG. 5, after the hollow interior 546 of the first reservoir 542 has been partially filled with the first liquid 502 as described heretofore, the first removable reservoir cap 550 is sealably fitted into the opening on the top of the first reservoir and the liquid weighing end of the first interconnecting air tube 506 is sealably connected to the first reservoir cap passageway 558 between the top and bottom of the first removable reservoir cap. A first tube passageway 562 exists between the interior 566 and exterior of the first elongated liquid tube 514, where this passageway is located on a side wall of the first elongated liquid tube near the top end thereof. The liquid processing end of the first interconnecting air tube 506 is sealably connected to the first tube passageway, thus allowing air to flow between the interior 566 of the first elongated liquid tube and the interior 546 of the first reservoir through the first interconnecting air tube. A first base passageway 570 also exists between the interior 566 and exterior of the first elongated liquid tube, where this passageway is located on the side wall of the first elongated liquid tube near the bottom end thereof. In the double-ring infiltrometer embodiment exemplified in FIG. 5 which includes the first support base 524, the first base passageway is located on this support base. The liquid processing end of the first interconnecting liquid tube 508 is sealably connected to the first base passageway.

Referring again to FIG. 5, the second surface-infiltrating bubbler unit includes a second elongated liquid tube 526, a second dispersive end cap 528, a second tube cap 530, and a second elongated air tube 532 which is slidably user-adjustable within the second elongated liquid tube. As exemplified in FIG. 5, an outer infiltration ring 534 has a prescribed interior diameter D2 and a prescribed height H3. The bottom end of the outer infiltration ring is axially embedded into the porous medium 500. In the double-ring infiltrometer embodiment exemplified in FIG. 5 the outer infiltration ring is substantially concentric with the inner infiltration ring 522, and the outer infiltration ring is axially embedded into the medium approximately the same depth D3 as the inner infiltration ring. The height H3 is greater than the depth D3 such that the top end of the outer infiltration ring axially extends above the top surface of the medium. Although the term "ring" is used to refer to the outer infiltration ring, it is noted that the outer infiltration ring can have a variety of radial cross-sectional shapes. In an exemplary embodiment of the double-ring infiltrometer described in this section, the outer infiltration ring has the same radial cross-sectional shape as the inner infiltration ring. An alternate embodiment of the double-ring infiltrometer is also possible where the inner and outer infiltration rings have different radial cross-sectional shapes.

Referring again to FIG. 5, the second surface-infiltrating bubbler unit is disposed on the top surface of the porous medium 500 in a region between the inner and outer infiltration rings 522 and 534 such that second dispersive the end cap 528 abuts the top surface of the medium and the bottom end of the second elongated air tube 532 is a prescribed distance H4 from the top surface of the medium. Generally speaking, the bottom end of the second elongated liquid tube 526 abuts the top surface of the second dispersive end cap. In the double-ring infiltrometer embodiment exemplified in FIG. 5, the bottom portion of the second elongated liquid tube tapers radially outward to form a second support base 536 for the second surface-infiltrating bubbler unit, and the bottom end of the second support base abuts the top surface of the second dispersive end cap. Having the second support base is advantageous since it serves to maintain the second surface-infiltrating bubbler unit in a substantially vertical position. It will be appreciated that an alternate embodiment of the double-ring infiltrometer (not shown) is also possible where the bottom portion of the second elongated liquid tube does not taper radially outward (i.e., there is no second support base on the second elongated liquid tube).

Referring again to FIG. 5, the second dispersive end cap 528 is perforated in order to allow the second liquid 504 to flow there-through. The second dispersive end cap serves to reduce the kinetic energy of the second liquid as it flows out of the second surface-infiltrating bubbler unit and into the region between the inner and outer infiltration rings 522 and 534, and vice versa, and thus serves to minimize erosion of the porous medium 500. The second tube cap 530 is sealably fitted onto the top end of the second elongated liquid tube 526. A second tube cap passageway 540 exists between the top and bottom of the second tube cap. The second elongated air tube 532 is sealably but slidably inserted into the second tube cap passageway such that the bottom end of the second elongated air tube extends a prescribed distance into the interior of the second elongated liquid tube and the top end of the second elongated air tube extends above the top of the second tube cap 530, where this distance can be adjusted by a user sliding the second elongated air tube up or down through the second tube cap passageway. The top end of the second elongated air tube is open to the in situ ambient air.

Referring again to FIG. 5, after the hollow interior 548 of the second reservoir 544 has been partially filled with the second liquid 504 as described heretofore, the second removable reservoir cap 552 is sealably fitted into the opening on the top of the second reservoir and the liquid weighing end of the second interconnecting air tube 510 is sealably connected to the second reservoir cap passageway 560 between the top and bottom of the second removable reservoir cap. A second tube passageway 564 exists between the interior 568 and exterior of the second elongated liquid tube 526, where this passageway is located on a side wall of the second elongated liquid tube near the top end thereof. The liquid processing end of the second interconnecting air tube 510 is sealably connected to the second tube passageway, thus allowing air to flow between the interior 568 of the second elongated liquid tube and the interior 548 of the second reservoir through the first interconnecting air tube. A second base passageway 572 also exists between the interior 568 and exterior of the second elongated liquid tube, where this passageway is located on the side wall of the second elongated liquid tube near the bottom end thereof. In the double-ring infiltrometer embodiment exemplified in FIG. 5 which includes the second support base 536, the second base passageway is located on this support base. The liquid processing end of the second interconnecting liquid tube 512 is sealably connected to the second base passageway.

Referring again to FIG. 5, the double-ring infiltrometer embodiment described in this section generally operates in the following manner. After the hollow interior 546 of the first reservoir 542 of the first liquid weighing subsystem has been partially filled with the first liquid 502, and the first liquid valve 574 on the first interconnecting liquid tube 508 has been opened (assuming this liquid tube includes this optional liquid valve), and the optional air valve (not shown) on the first interconnecting air tube 506 has also been opened (assuming this air tube includes this air valve), the first liquid will flow from the interior 546 of the first reservoir, through the first reservoir passageway 582, through the first interconnecting liquid tube, through the first base passageway 570, into the lower end of the interior 566 of the first elongated liquid tube 514, through the first dispersive end cap 516, and into the interior of the inner infiltration ring 522 until a first constant liquid head is established in the interior of the inner infiltration ring. As exemplified in FIG. 5, the first constant liquid head has a first height which is equal to the distance H1 between the bottom end of the first elongated air tube 520 and the top surface of the porous medium 500. The first height of the first constant liquid head can be increased by a user sliding the first elongated air tube up through the first tube cap passageway 538, and can be decreased by the user sliding the first elongated air tube down through the first tube cap passageway. Similarly, after the hollow interior 548 of the second reservoir 544 of the second liquid weighing subsystem has been partially filled with the second liquid 504, and the second liquid valve 576 on the second interconnecting liquid tube 512 has been opened (assuming this liquid tube includes this optional liquid valve), and the optional air valve (not shown) on the second interconnecting air tube 510 has also been opened (assuming this air tube includes this air valve), the second liquid will flow from the interior 548 of the second reservoir, through the second reservoir passageway 584, through the second interconnecting liquid tube, through the second base passageway 572, into the lower end of the interior 568 of the second elongated liquid tube 526, through the second dispersive end cap 528, and into the region between the inner and outer infiltration rings 522 and 534 until a second constant liquid head is established in this region. As exemplified in FIG. 5, the second constant liquid head has a second height which is equal to the distance H4 between the bottom end of the second elongated air tube 532 and the top surface of the medium. The second height of the second constant liquid head can be increased by the user sliding the second elongated air tube up through the second tube cap passageway 540, and can be decreased by the user sliding the second elongated air tube down through the second tube cap passageway. In an exemplary embodiment of the double-ring infiltrometer the distance H1 is set to be equal to the distance H4, and a value of approximately 4 inches is used for both.

Referring again to FIG. 5 and with regard to the first liquid weighing subsystem and first surface-infiltrating bubbler unit, it will be appreciated that as the first liquid 502 flows into the into the interior of the inner infiltration ring 522 a partial vacuum is established in the hollow interior 546 of the first reservoir 542 which causes the first liquid to rise up into the interior 566 of the first elongated liquid tube 514 until the height of the first liquid within the first elongated liquid tube is approximately the same as the height of the first liquid within the first reservoir. Similarly, with regard to the second liquid weighing subsystem and second surface-infiltrating bubbler unit, it will be appreciated that as the second liquid 504 flows into the region between the inner and outer infiltration rings 522 and 534 a partial vacuum is established in the hollow interior 548 of the second reservoir 544 which causes the second liquid to rise up into the interior 568 of the second elongated liquid tube 526 until the height of the second liquid within the second elongated liquid tube is approximately the same as the height of the second liquid within the second reservoir.

Referring again to FIG. 5, the double-ring infiltrometer embodiment described in this section serves to maintain the height of the first liquid 502 in the interior of the inner infiltration ring 522 at the distance H1. In other words, as the first liquid in the interior of the inner infiltration ring infiltrates into the porous medium 500 additional first liquid will flow from the hollow interior 546 of the first reservoir 542, through the first interconnecting liquid tube 508, and into the interior of the inner infiltration ring in order to maintain the height of the first liquid head therein at the distance H1. Similarly the double-ring infiltrometer embodiment serves to maintain the height of the second liquid 504 in the region between the inner and outer infiltration rings 522 and 534 at the distance H4. In other words, as the second liquid in the region between the inner and outer infiltration rings infiltrates into the medium additional second liquid will flow from the hollow interior 548 of the second reservoir 544, through the second interconnecting liquid tube 512, and into this region in order to maintain the height of the second liquid head therein at the distance H4.

Referring again to FIG. 5 and as described heretofore, with regard to the first liquid weighing subsystem, the first weighing device 578 continuously measures the weight of the first liquid 502 in the first reservoir 542, and the first data processing device 554 routinely reads and stores the weight measurements. The first data processing device can analyze the stored weight measurements on an ongoing basis to determine when a first prescribed steady-state liquid flow rate condition has been reached. Once this condition has been reached, the first data processing device can further analyze the stored weight measurements to compute the saturated hydraulic conductivity of the porous medium 500 that is within the interior of the inner infiltration ring 522. Similarly and with regard to the second liquid weighing subsystem, the second weighing device 580 continuously measures the weight of the second liquid 504 in the second reservoir 544, and the second data processing device 556 routinely reads and stores the weight measurements. The second data processing device can analyze the stored weight measurements on an ongoing basis to determine when a second prescribed steady-state liquid flow rate condition has been reached (where this second condition may or may not be the same as the first prescribed steady-state liquid flow rate condition). Once this second condition has been reached, the second data processing device can further analyze the stored weight measurements to compute the saturated hydraulic conductivity of the medium in the region between the inner and outer infiltration rings 522 and 534. As is appreciated in the arts of soil science and hydrology, the presence of the outer infiltration ring and the second liquid in the region between the inner and outer infiltration rings are advantageous since they minimize the lateral flow of the first liquid in the interior of the inner infiltration ring (e.g., they cause the first liquid to flow nearly exclusively downward), which simplifies the analysis of the weight measurements and reduces any error that may result therein.

Referring again to FIG. 5, the dimensions and radially cross-sectional shape of the first elongated liquid tube 514, second elongated liquid tube 526, first elongated air tube 520, and second elongated air tube 532 are generally the same as those described heretofore for the first permeameter embodiment. As such, the first elongated air tube can be slidably adjusted by a user to a downward-most position in which the bottom end of this air tube abuts the top surface of the first dispersive end cap 516 while the top end of this air tube still extends above the top of the first tube cap 518. Similarly, the second elongated air tube can be slidably adjusted by the user to a downward-most position in which the bottom end of this air tube abuts the top surface of the second dispersive end cap 528 while the top end of this air tube still extends above the top of the second tube cap 530. Similarly, the materials used to construct the first elongated liquid tube 514, second elongated liquid tube 526, first elongated air tube 520, second elongated air tube 532, first tube cap, second tube cap, first dispersive end cap 516, and second dispersive end cap 528 are generally the same as those described heretofore for the first permeameter embodiment. The inner and outer infiltration rings 522 and 534 can be constructed from any material which is inert, impervious to the first liquid 502 and second liquid 504, and is capable of being forcibly embedded into the porous medium 500. By way of example but not limitation, the inner and outer infiltration rings can be constructed from stainless steel.

Referring again to FIG. 5, it will be appreciated that the inner infiltration ring 522 can have any interior diameter D1 that is large enough to allow the first surface-infiltrating bubbler unit to be disposed there-within. The outer infiltration ring 534 can have any interior diameter D2 that is large enough to allow the second surface-infiltrating bubbler unit to be disposed in the region between the inner and outer infiltration rings. The depth D3 to which the inner and outer infiltration rings are axially embedded into the porous medium 500 can have various values. The inner infiltration ring can have any height H2 which is greater than the sum of depth D3 and distance H1, and is also greater than the sum of depth D3 and distance H4. The outer infiltration ring can have any height H3 which is greater than the sum of depth D3 and distance H4. The particular interior diameter D1, interior diameter D2, depth D3, height H2, height H3, distance H1 and distance H4 that are used are generally application dependent and are selected based on the dimensions of the first and second surface-infiltrating bubbler units, the type of medium that is being tested, and the particular hydraulic properties of the medium that are being measured, among other things. In an exemplary embodiment of the double-ring infiltrometer described in this section the inner infiltration ring has an interior diameter D1 of approximately 12 inches, the outer infiltration ring has an interior diameter D2 of approximately 24 inches, the inner and outer infiltration rings are axially embedded into the medium a depth D3 of approximately 3 inches, the inner infiltration ring has a height H2 of approximately 10 inches, and the outer infiltration ring has a height H3 of approximately 10 inches.

1.5 Automated Constant Head Pressure Infiltrometer

Figure 6:
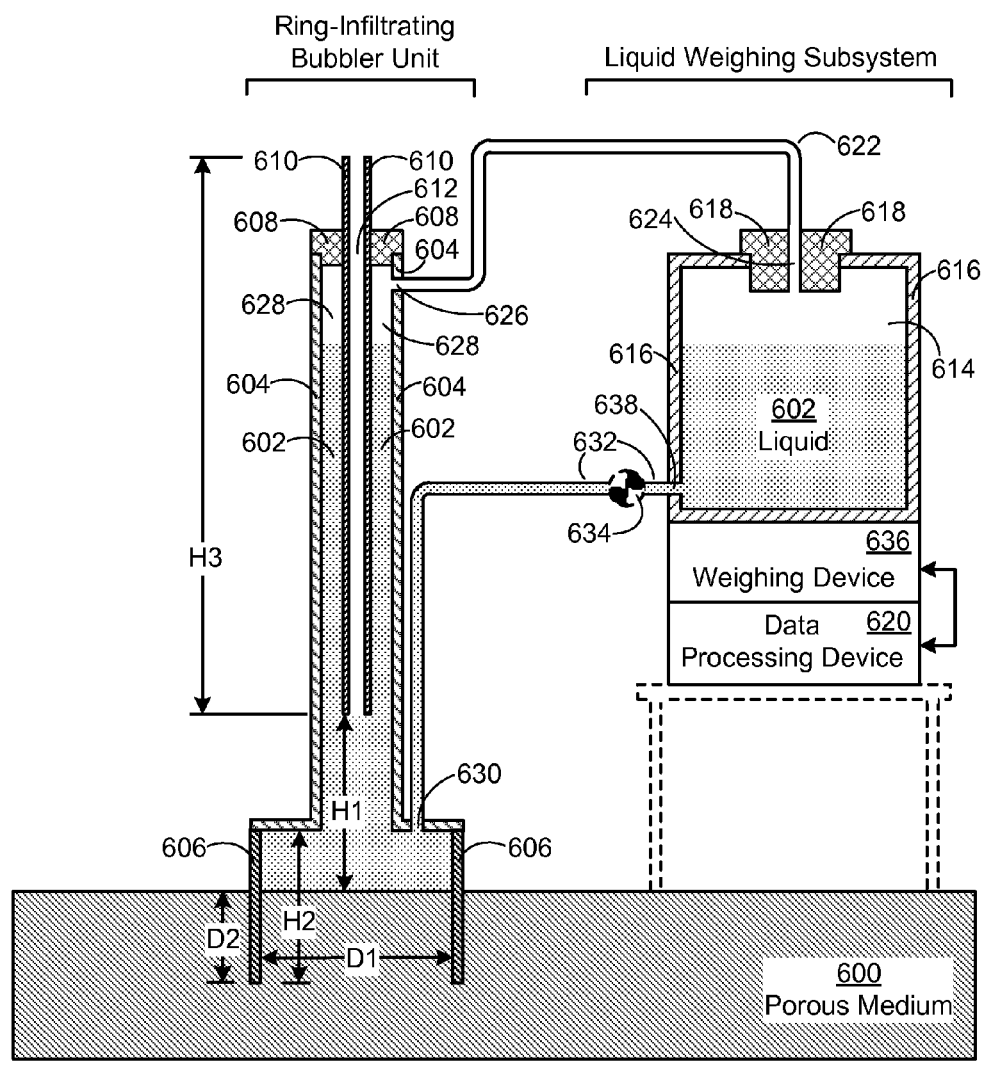
FIG. 6 is a diagram illustrating a front elevational view, in simplified form and partly in cross-section, of an exemplary automated constant head pressure infiltrometer implementation of the apparatus embodiments described herein.

FIG. 6 illustrates a front elevational view, in simplified form and partly in cross-section, of an exemplary automated constant head pressure infiltrometer implementation of the apparatus embodiments described herein (hereafter simply referred to as the "pressure infiltrometer embodiment"). The pressure infiltrometer embodiment exemplified in FIG. 6 can be used to measure various hydraulic properties of the porous medium 600 such as the saturated hydraulic conductivity of the medium, among others. In the pressure infiltrometer embodiment described in this section the liquid weighing subsystem is implemented in the manner described heretofore. The liquid processing subsystem is a modified version of a conventional Mariotte bubbler which is hereafter simply referred to as a "ring-infiltrating bubbler unit." As will be described in more detail hereafter, the liquid weighing subsystem is sealably connected to the ring-infiltrating bubbler unit via both an interconnecting air tube 622 and an interconnecting liquid tube 632. It will be appreciated that the pressure infiltrometer embodiment is useful in applications where liquid ponding and infiltration are factors of interest in preventing the liquid from infiltrating the medium (e.g., the desire is to retain the liquid on top of the medium).

As exemplified in FIG. 6, the ring-infiltrating bubbler unit includes an elongated liquid tube 604, an infiltration ring 606, a tube cap 608, and an elongated air tube 610 which is slidably user-adjustable within the interior of the elongated liquid tube. The infiltration ring has a prescribed interior diameter D1 and a prescribed height H2, and is axially embedded into the porous medium 600 a prescribed depth D2, where the depth D2 is less than or equal to the height H2 such that the top end of the infiltration ring either axially extends above the top surface of the medium, or is axially flush with the top surface of the medium. Although the term "ring" is used to refer to the infiltration ring, it is noted that the infiltration ring can have a variety of radial cross-sectional shapes. In an exemplary embodiment of the pressure infiltrometer described in this section, the infiltration ring has a substantially circular radial cross-sectional shape. Alternate embodiments of the pressure infiltrometer are also possible where the infiltration ring has a radial cross-sectional shape which is either substantially square, or substantially hexagonal, among other shapes.

Generally speaking and referring again to FIG. 6, the bottom end of the elongated liquid tube 604 is sealably attached to the top end of the infiltration ring 606. More particularly and by way of example but not limitation, in the pressure infiltrometer embodiment exemplified in FIG. 6 where the interior diameter D1 of the infiltration ring is greater than the interior diameter of the elongated liquid tube, the bottom portion of the elongated liquid tube tapers radially outward and the bottom end of the elongated liquid tube is sealably attached to the top end of the infiltration ring. As such, the infiltration ring serves as a support base for the ring-infiltrating bubbler unit which maintains the bubbler unit in a substantially vertical position. The tube cap 608 is sealably fitted onto the top end of the elongated liquid tube. A tube cap passageway 612 exists between the top and bottom of the tube cap. The elongated air tube 610 is sealably but slidably inserted into the tube cap passageway such that the bottom end of the elongated air tube extends into the interior of the elongated liquid tube, the bottom end of the elongated air tube is a prescribed distance H1 from the top surface of the porous medium 600, and the top end of the elongated air tube extends above the top of the tube cap, where the distance H1 can be adjusted by a user sliding the elongated air tube up or down through the tube cap passageway. The top end of the elongated air tube is open to the in situ ambient air.

Referring again to FIG. 6, after the hollow interior 614 of the reservoir 616 has been partially filled with the liquid 602 as described heretofore, the removable reservoir cap 618 is sealably fitted into the opening on the top of the reservoir and the liquid weighing end of the interconnecting air tube 622 is sealably connected to the reservoir cap passageway 624 between the top and bottom of the reservoir cap. A tube passageway 626 exists between the interior 628 and exterior of the elongated liquid tube 604, where this passageway is located on a side wall of the elongated liquid tube near the top end thereof. The liquid processing end of the interconnecting air tube is sealably connected to the tube passageway, thus allowing air to flow between the interior of the elongated liquid tube and the interior of the reservoir through the interconnecting air tube. A base passageway 630 also exists between the interior and exterior of the elongated liquid tube, where this passageway is located on the sidewall of the elongated liquid tube near the bottom end thereof. The liquid processing end of the interconnecting liquid tube 632 is sealably connected to the base passageway.

Referring again to FIG. 6, the pressure infiltrometer embodiment described in this section generally operates in the following manner. After the hollow interior 614 of the reservoir 616 has been partially filled with the liquid 602, and the liquid valve 634 on the interconnecting liquid tube 632 has been opened (assuming this liquid tube includes this optional liquid valve), and the optional air valve (not shown) on the interconnecting air tube 622 has also been opened (assuming this air tube includes this air valve), the liquid will flow from the interior of the reservoir, through the reservoir passageway 638, through the interconnecting liquid tube, through the base passageway 630, and into the interior of the infiltration ring 606 and the interior 628 of the elongated liquid tube 604 until a constant liquid head is established therein. As exemplified in FIG. 6, this head has a height which is equal to the distance H1 between the bottom end of the elongated air tube 610 and the top surface of the porous medium 600. It will be appreciated that the height of the constant liquid head can be increased by a user sliding the elongated air tube up through the tube cap passageway 612, and can be decreased by the user sliding the elongated air tube down through the tube cap passageway. In an exemplary embodiment of the pressure infiltrometer the distance H1 is approximately 6 inches. It will be appreciated that as the liquid flows into the interior of the infiltration ring a partial vacuum is established in the interior of the reservoir which causes the liquid to rise up into the interior of the elongated liquid tube until the height of the liquid within the elongated liquid tube is approximately the same as the height of the liquid within the reservoir.

Referring again to FIG. 6, the pressure infiltrometer embodiment described in this section serves to maintain the height of the liquid head in the interior 628 of the elongated liquid tube 604 at the distance H1. In other words, as the liquid 602 in the interior of the infiltration ring 606 infiltrates into the porous medium 600 additional liquid will flow from the hollow interior 614 of the reservoir 616, through the interconnecting liquid tube 632, and into the interior of the infiltration ring in order to maintain the height of the liquid head in the interior of the elongated liquid tube at the distance H1. Thus, the pressure infiltrometer embodiment serves to establish a constant liquid head pressure on the top surface of the medium that is within the interior of the infiltration ring.

Referring again to FIG. 6 and as described heretofore, the weighing device 636 continuously measures the weight of the liquid 602 in the reservoir 616, and the data processing device 620 routinely reads and stores the weight measurements. The data processing device can analyze the stored weight measurements on an ongoing basis to determine when a prescribed steady-state liquid flow rate condition has been reached. Once this condition has been reached, the data processing device can further analyze the stored weight measurements to compute the saturated hydraulic conductivity of the portion of the porous medium 600 that is within the interior of the infiltration ring 606.

Referring again to FIG. 6, the dimensions and radially cross-sectional shape of the ring-infiltrating bubbler unit's elongated liquid tube 604, and the interior diameter of the elongated air tube 610 are generally the same as those described heretofore for the first permeameter embodiment. The elongated air tube has a prescribed height H3 which is large enough to allow the elongated air tube to be slidably adjusted by a user to a downward-most position in which the bottom end of the elongated air tube abuts the top surface of the porous medium 600 while the top end of the elongated air tube still extends above the top of the tube cap 608. It will be appreciated that the infiltration ring 606 can have various interior diameters D1 and heights H2. The depth D2 to which the infiltration ring is axially embedded into the medium can have various values. The particular interior diameter D1, height H2 and depth D2 that are used are generally application dependent and are selected based on the dimensions of the ring-infiltrating bubbler unit, the type of medium that is being tested, and the particular hydraulic properties of the medium that are being measured, among other things. In an exemplary embodiment of the pressure infiltrometer described in this section the infiltration ring has an interior diameter D1 of approximately 8 inches, a height H2 of approximately 2.5 inches, and is axially embedded into the medium a depth D2 of approximately 1.5 inches. The materials used to construct the elongated liquid tube, elongated air tube, and tube cap are generally the same as those described heretofore for the first permeameter embodiment. The material used to construct the infiltration ring is generally the same as that described heretofore for the double-ring infiltrometer embodiment.

1.6 Automated Constant Head Tension Infiltrometer

Figure 7:
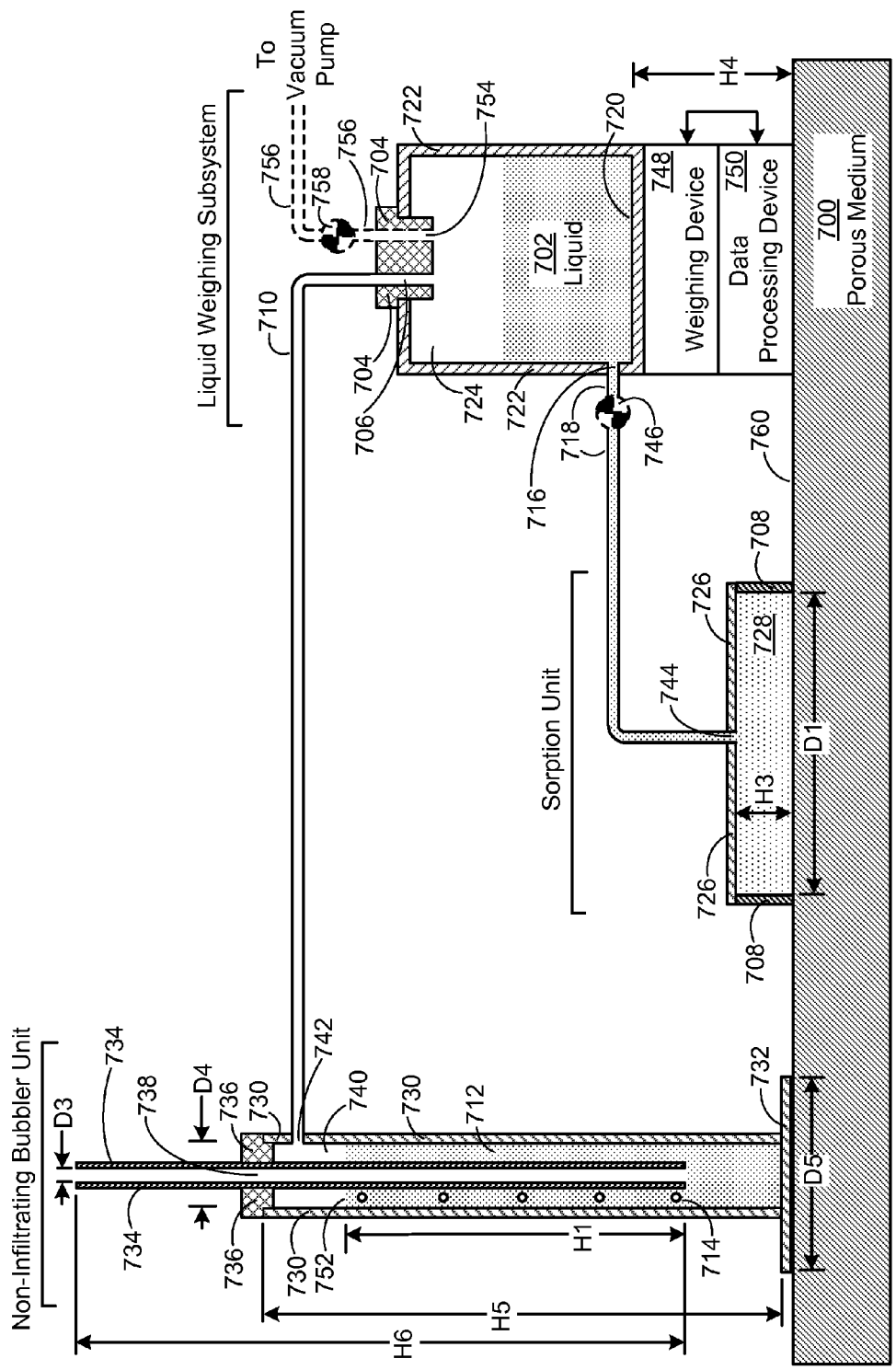
FIG. 7 is a diagram illustrating a front elevational view, in simplified form and partly in cross-section, of an exemplary automated constant head tension infiltrometer implementation of the apparatus embodiments described herein.

FIG. 7 illustrates a front elevational view, in simplified form and partly in cross-section, of an exemplary automated constant head tension infiltrometer implementation of the apparatus embodiments described herein (hereafter simply referred to as the "tension infiltrometer embodiment"). The tension infiltrometer embodiment exemplified in FIG. 7 can be used to measure various hydraulic properties of the porous medium 700 such as the sorptivity of the medium, among others. As is appreciated in the arts of soil science and hydrology, the sorptivity of the medium is a measure of the capacity of the medium to sorb a liquid by capillary action (e.g., the medium either adsorbs the liquid, or absorbs the liquid, or both). Thus, the tension infiltrometer embodiments described in this section can continuously measure the sorptive characteristics of the medium. In the tension infiltrometer embodiment exemplified in FIG. 7, the liquid weighing subsystem is implemented in the manner described heretofore. The liquid processing subsystem generally includes two different components, namely a modified version of a conventional Mariotte bubbler which is hereafter simply referred to as a "non-infiltrating bubbler unit", and a "sorption unit", both of which will be described in more detail hereafter. As will also be described in more detail hereafter, the liquid weighing subsystem is sealably connected to the bubbler unit via an interconnecting air tube 710. The liquid weighing subsystem is sealably connected to the sorption unit via an interconnecting liquid tube 718.

Referring again to FIG. 7, the non-infiltrating bubbler unit includes an elongated liquid tube 730, a non-porous base 732, a removable tube cap 736, and an elongated air tube 734 which is slidably user-adjustable within the interior 740 of the elongated liquid tube. The base has a diameter D5 which is either equal to or greater than the exterior diameter of the elongated liquid tube. The bottom end of the elongated liquid tube is sealably attached to the top surface of the base such that the base serves to sealably close the bottom end of the elongated liquid tube. The base also serves to maintain the bubbler unit in a substantially vertical position. The tube cap is sealably fitted onto the top end of the elongated liquid tube. A tube cap passageway 738 exists between the top and bottom of the tube cap. The elongated air tube is sealably but slidably inserted into the tube cap passageway such that the bottom end of the elongated air tube extends a prescribed distance H1 beneath the top surface 752 of a liquid 712 that resides within the interior 740 of the elongated liquid tube, and the top end of the elongated air tube extends above the top of the tube cap, where the distance H1 can be adjusted by a user sliding the elongated air tube up or down through the tube cap passageway. The top end of the elongated air tube is open to the in situ ambient air.

Referring again to FIG. 7, a tube passageway 742 exists between the interior 740 and exterior of the elongated liquid tube 730, where this passageway is located on a side wall of the elongated liquid tube near the top end thereof. When the tension infiltrometer embodiment described in this section is initially placed into operational use in situ, the removable tube cap 736 is removed from the top end of the elongated liquid tube and the interior of the elongated liquid tube is partially filled with the liquid 712 such that the top surface 752 of the liquid 712 is close to but still beneath the tube passageway (e.g., two inches, among other distances, beneath the tube passageway). In an exemplary embodiment of the tension infiltrometer described in this section the liquid 712 that partially fills the interior 740 of the elongated liquid tube is the same as the liquid 702 that is in the reservoir 722. It is noted however that an alternate embodiment of the tension infiltrometer is also possible where the liquid 712 that partially fills the interior 740 of the elongated liquid tube is different than the liquid 702 that is in the reservoir.

Referring again to FIG. 7, the sorption unit includes an infiltration ring 708, a top cover 726, and a porous sensing element 728. The infiltration ring has a prescribed interior diameter D1 and a prescribed height H3, and is disposed on the top surface 760 of the porous medium 700. Although the term "ring" is used to refer to the infiltration ring, it is noted that the infiltration ring can have a variety of radial cross-sectional shapes. In an exemplary embodiment of the tension infiltrometer described in this section, the infiltration ring has a substantially circular radial cross-sectional shape. Alternate embodiments of the tension infiltrometer are also possible where the infiltration ring has a radial cross-sectional shape which is either substantially square, or substantially hexagonal, among other shapes. The top cover is sealably attached to the top end of the infiltration ring. A cover passageway 744 exists between the top and bottom of the top cover. The sensing element is disposed in the space bounded by the bottom surface of the top cover, the top surface of the medium, and the axially inner surface of the infiltration ring. As exemplified in FIG. 7, the sensing element has a diameter which is approximately equal to the diameter D1 and a height which is approximately equal to the height H3. The sensing element also has the same radial cross-sectional shape as the infiltration ring. Thus, the sensing element is sized and shaped such that it substantially fills the just described space.

Referring again to FIG. 7, after the hollow interior 724 of the reservoir 722 has been partially filled with the liquid 702 as described heretofore, the removable reservoir cap 704 is sealably fitted into the opening on the top of the reservoir and the liquid weighing end of the interconnecting air tube 710 is sealably connected to the reservoir cap passageway 706. The liquid processing end of the interconnecting air tube is sealably connected to the tube passageway 742 on the elongated liquid tube 730, thus allowing air to flow between the interior 740 of the elongated liquid tube and the interior 724 of the reservoir through the interconnecting air tube. The liquid processing end of the interconnecting liquid tube 718 is sealably connected to the cover passageway 744 on the top cover 726.

Referring again to FIG. 7, the tension infiltrometer embodiment described in this section generally operates in the following manner. After the hollow interior 724 of the reservoir 722 has been partially filled with the liquid 702, and the interior 740 of the elongated liquid tube 730 has been partially filled with the liquid 712, and the liquid valve 746 on the interconnecting liquid tube 718 has been opened (assuming this tube includes this optional valve), and the optional air valve (not shown) on the interconnecting air tube 710 has also been opened (assuming this air tube includes this air valve), the liquid 702 will flow from the interior 724 of the reservoir, through the reservoir passageway 716, through the interconnecting liquid tube, through the cover passageway 744, and into the porous sensing element 728. The sensing element has a continuous, interconnected system of pores which is permeable to the liquid 702, among other things. As such, the liquid 702 will flow into the pores of the sensing element, and the bottom surface of the sensing element will provide a wetted surface which is in liquid contact with the top surface 760 of the porous medium 700. As a result, the liquid 702 will be sorbed (e.g., "wicked") from the sensing element into the top surface of the medium by capillary action (e.g., the liquid 702 will be naturally pulled via capillary action from the pores of the sensing element and will flow into the top surface of the medium) until the liquid 702 content within the medium and the liquid content within the sensing element are equalized. As the liquid 702 is sorbed into the top surface of the medium, additional liquid 702 will flow from the interior 724 of the reservoir, through the interconnecting liquid tube, through the cover passageway, and into the pores of the sensing element in order to replace the liquid 702 that is sorbed. As is appreciated in the art of tension infiltrometers, the non-infiltrating bubbler unit serves to establish and maintain a negative pressure (i.e., a partial vacuum) in the interior 724 of the reservoir, where this negative pressure results in the liquid 702 being supplied to the top surface of the medium under a constant liquid tension (e.g., a constant negative head) which prevents gravity from affecting the liquid 702 flow into the medium (e.g., the liquid is sorbed into the medium just through the wicking/capillary action).

Referring again to FIG. 7, the radially cross-sectional shape and interior diameter of the non-infiltrating bubbler unit's elongated liquid tube 730, and the interior diameter of the elongated air tube 734 are generally the same as those described heretofore for the first permeameter embodiment. The elongated liquid tube has a prescribed height H5 which is generally application dependent and can have various values. In an exemplary embodiment of the tension infiltrometer described in this section the elongated liquid tube has a height H5 of approximately 2 feet. The elongated air tube has a prescribed height H6 which is large enough to allow the elongated air tube to be slidably adjusted by a user to a downward-most position in which the bottom end of the elongated air tube abuts the top surface of the non-porous base 732 while the top end of the elongated air tube still extends above the top of the removable tube cap 736. It will be appreciated that the infiltration ring 708 can have various interior diameters D1 and heights H3. The particular interior diameter D1 and height H3 that are used are generally application dependent and are selected based on the type of medium that is being tested and the porosity characteristics of the porous sensing element 728 that is being used, among other things. In an exemplary embodiment of the tension infiltrometer the infiltration ring has an interior diameter D1 of approximately 7.8 inches and a height H3 of approximately 4.5 inches.

Referring again to FIG. 7 and as is appreciated in the art of tension infiltrometers, the amount of negative pressure in the hollow interior 724 of the reservoir 722 (and thus the amount of liquid tension that exists on the liquid 702 being supplied to the top surface 760 of the porous medium 700) can be increased by sliding the elongated air tube 734 down through the tube cap passageway 738 so as to increase the distance H1 the elongated air tube extends beneath the top surface 752 of the liquid 712 in the elongated liquid tube 730, and can be decreased by sliding the elongated air tube up through the tube cap passageway so as to decrease this distance H1. In other words, given that H4 is the vertical distance between the top surface of the medium and the bottom surface 720 of the interior 724 of the reservoir, the degree of negative pressure p in the interior 724 of the reservoir can given by the equation $p=-(H1-H4)$. As is also appreciated in the art of tension infiltrometers, despite the fact that the amount of liquid 702 in the interior 724 of the reservoir will be reduced as the liquid 702 is sorbed into the top surface of the medium, the liquid tension that exists on the liquid 702 (and hence the negative pressure that exists in the interior 724 of the reservoir) will remain constant since this tension is regulated by the non-infiltrating bubbler unit. In the aforementioned exemplary embodiment of the tension infiltrometer described in this section where the elongated liquid tube has a height H5 of approximately 2 feet, distance H4 has a value of approximately 8 inches and distance H1 has a value in the range of approximately zero inches to 10 inches, which results in the liquid tension having a value in the range of approximately zero psi (pounds per square inch) to 0.37 psi.

Referring again to FIG. 7 and as described heretofore, the weighing device 748 continuously measures the weight of the liquid 702 in the reservoir 722, and the data processing device 750 routinely reads and stores the weight measurements. The data processing device can analyze the stored weight measurements on an ongoing basis to compute the rate of sorption of the liquid 702 over time. The data processing device can then use this rate of sorption to also compute a sorptivity value for the porous medium 700.

Referring again to FIG. 7, the materials used to construct the elongated liquid tube 730, elongated air tube 734, and removable tube cap 736 are generally the same as those described heretofore for the first permeameter embodiment. The non-porous base 732 and top cover 726 can be constructed from any material which is substantially rigid, inert and impervious to the liquid 712 and liquid 702 respectively. By way of example but not limitation, the base and top cover can be constructed from either plastic, or glass, or a non-porous ceramic. The material used to construct the infiltration ring 708 is generally the same as that described heretofore for the double-ring infiltrometer embodiment. The porous sensing element 728 can be made from various types of porous and inert materials having various pore sizes. In an exemplary embodiment of the tension infiltrometer described in this section the sensing element is made from a porous ceramic material.

Generally speaking and referring again to FIG. 7, the tension infiltrometer embodiment described in this section can optionally be sealably connected to a vacuum pump (not shown) which can optionally be used to initially calibrate the embodiment. More particularly, another reservoir cap passageway 754 can exist between the top and bottom of the removable reservoir cap 704. A liquid weighing end of another interconnecting air tube 756 can be sealably connected to the cap passageway 754. A pump end of the interconnecting air tube 756 can be sealably connected to the vacuum pump. The interconnecting air tube 756 can include an air valve 758 which generally operates to control the flow of air in the interconnecting air tube 756. More particularly, whenever the reservoir cap is sealably fitted into the opening on the top of the reservoir 722 and the air valve is open, air can freely flow between the vacuum pump and the hollow interior 724 of the reservoir through the interconnecting air tube 756 and cap passageway 754. Whenever the reservoir cap is sealably fitted into the opening on the top of the reservoir and the air valve is closed, no air can flow between the vacuum pump and the interior 724 of the reservoir (i.e., the closure of the air valve effectively serves to sealably close the cap passageway 754).

Referring again to FIG. 7, the following is a brief description of how the vacuum pump can be used to initially calibrate the tension infiltrometer embodiment described in this section. A conventional manometer (not shown) can be temporarily sealably connected to the reservoir passageway 716. The air valve 758 can then be opened and the vacuum pump can be turned on until bubbles 714 appear in the liquid 712 within the interior 740 of the elongated liquid tube 730. This serves to establish an initial partial vacuum within the hollow interior 724 of the reservoir 722. The air valve can then be closed and the manometer can be read to determine the current pressure of the liquid 702. If the current pressure of the liquid is not equal to a desired value (e.g., 10 centibars), this pressure can be user-adjusted to the desired value by adjusting the distance H1 until the desired value is indicated on the manometer.

2.0 Additional Embodiments

While the hydraulic property measurement apparatus has been described by specific reference to embodiments thereof, it is understood that variations and modifications thereof can be made without departing from the true spirit and scope of the apparatus. By way of example but not limitation, in the automated constant head tension infiltrometer implementation of the apparatus embodiments described herein, rather than the infiltration ring being disposed on the top surface of the porous medium as described heretofore, the ring can also have a larger height such that a bottom portion of the ring extends below the bottom surface of the sensing element a prescribed distance, and this bottom portion can be axially embedded into the medium until the bottom surface of the sensing element makes contact with the top surface of the medium.

Additionally, in the automated constant head double ring infiltrometer implementation of the apparatus embodiments described herein, since the liquid weight measurements made by the second liquid weighing subsystem may generally just be used to determine when the second constant liquid head is established in the region between the inner and outer infiltration rings (i.e., it may be unnecessary to determine the rate of consumption of the second liquid), the second surface-infiltrating bubbler unit can be replaced with other types of liquid processing subsystems which operate cooperatively with the second liquid weighing subsystem to maintain the second constant liquid head at a prescribed height. By way of example but not limitation, an alternate embodiment of the double ring infiltrometer implementation is possible where, rather than employing the second surface-infiltrating bubbler unit, the liquid processing end of the second interconnecting liquid tube can be sealably connected to a conventional floating-valve-type liquid supply unit which is mounted on the top end of the outer infiltration ring. An alternate implementation of this particular embodiment is also possible where, rather than employing the second liquid weighing subsystem, the liquid weighing end of the second interconnecting liquid tube can be connected to a conventional water supply tap. Another alternate embodiment of the double ring infiltrometer implementation is also possible where, rather than employing the first surface-infiltrating bubbler unit, the liquid processing end of the first interconnecting liquid tube can be sealably connected to another floating-valve-type liquid supply unit which is mounted on the top end of the inner infiltration ring.

It is also noted that any or all of the aforementioned embodiments can be used in any combination desired to form additional hybrid embodiments. Although the apparatus embodiments have been described in language specific to structural features and/or methodological acts, it is to be understood that the subject matter defined in the appended claims is not necessarily limited to the specific features or acts described heretofore. Rather, the specific features and acts described heretofore are disclosed as example forms of implementing the claims.

Wherefore, what is claimed is:

1. An apparatus for testing a porous medium, comprising:
a first liquid processing subsystem which is interfaced with the medium in a manner that establishes liquid contact between the first liquid processing subsystem and the medium; and
a first liquid weighing subsystem, wherein,
the first liquid processing and first liquid weighing subsystems are sealably interconnected via a first interconnecting liquid tube,
the first liquid weighing subsystem stores a first liquid,
the first liquid flows from the first liquid weighing subsystem, through the first interconnecting liquid tube, through the first liquid processing subsystem, and into the medium until the medium is saturated with the first liquid, and
the first liquid weighing subsystem automatically measures the weight of the first liquid stored therein on an ongoing basis and uses said liquid weight measurements to determine one or more hydraulic properties of the medium.

2. The apparatus of claim 1, wherein the first liquid weighing subsystem comprises:
a reservoir comprising,
a hollow interior which is partially filled with the first liquid,
an opening on a top of the reservoir, and
a reservoir passageway between said interior and an exterior of the reservoir, wherein the reservoir passageway is located on a side wall of the reservoir near a bottom surface of said interior, and one end of the first interconnecting liquid tube is sealably connected to the reservoir passageway;
a weighing device comprising a first data port, wherein the reservoir is centrally disposed on top of the weighing device, and the weighing device continuously measures the weight of the first liquid within the reservoir; and
a data processing device comprising a second data port, wherein the first and second data ports are interconnected via a data connection, the data processing device uses the data connection to routinely read the weight measurements made by the weighing device, the data processing device stores each of the read weight measurements in a time and date stamped format, the data processing device analyzes the stored weight measurements on an ongoing basis to compute changes in the amount of the first liquid within the reservoir over time, and from said changes the data processing device computes the one or more hydraulic properties of the medium.

3. The apparatus of claim 2, wherein the first liquid weighing subsystem further comprises an elevating device which is used to provide a stable and level platform for the reservoir and weighing device, and is also used to elevate the reservoir to create a prescribed amount of overhead pressure in the apparatus.

4. The apparatus of claim 2, wherein the reservoir further comprises an interior liquid volume of 8 liters, and the weighing device further comprises a digital scale comprising a maximum weight capacity of 10 kilograms.

5. The apparatus of claim 2, wherein the data processing device further comprises one or more of:
a third data port to which a removable data storage device is connected; or
Global Positioning System functionality; or
alarm functionality.

6. The apparatus of claim 2, wherein,
the first liquid processing subsystem comprises a borehole liquid level stabilization device comprising a floating valve,
the stabilization device is adjustably suspended at a prescribed depth within a borehole that is formed in the porous medium,
the opening on the top of the reservoir is open to in situ ambient air,
the other end of the first interconnecting liquid tube is sealably connected to the stabilization device,
the first liquid flows from the hollow interior of the reservoir, through the reservoir passageway, through the first interconnecting liquid tube, through the stabilization device, and into the borehole until a constant liquid head having a prescribed height is established at a bottom of the borehole,
the floating valve serves to control the flow rate of the first liquid into the borehole in order to maintain the constant liquid head at said height, and
the one or more hydraulic properties of the medium comprise the saturated hydraulic conductivity of the medium.

7. The apparatus of claim 2, wherein,
the first liquid weighing subsystem further comprises a removable reservoir cap comprising a reservoir cap passageway between a top of the reservoir cap and a bottom of the reservoir cap,
the reservoir cap is sealably fitted into the opening on the top of the reservoir,
one end of an interconnecting air tube is sealably connected to the reservoir cap passageway,
the first liquid processing subsystem comprises a borehole bubbler unit comprising an elongated liquid tube, a dispersive end cap which is perforated to allow the first liquid to flow there-through, a tube cap comprising a tube cap passageway between a top of the tube cap and a bottom of the tube cap, and an elongated air tube,
the elongated liquid tube comprises a tube passageway between an interior and an exterior of the elongated liquid tube, the tube passageway being located on a side wall of the elongated liquid tube near a top end thereof,
the other end of the interconnecting air tube is sealably connected to the tube passageway,
the tube cap is sealably fitted onto the top end of the elongated liquid tube,
the elongated air tube is sealably but slidably inserted into the tube cap passageway such that a bottom end of the elongated air tube extends into the interior of the elongated liquid tube and a top end of the elongated air tube extends above the top of the tube cap,
the top end of the elongated air tube is open to in situ ambient air,
the bubbler unit is inserted into a borehole that is formed in the porous medium such that the end cap abuts a bottom of the borehole and a bottom end of the elongated liquid tube abuts a top surface of the end cap,
the other end of the first interconnecting liquid tube is inserted into the borehole next to the elongated liquid tube such that said other end either abuts or is substantially near the top surface of the end cap,
the first liquid flows from the hollow interior of the reservoir, through the reservoir passageway, through the first interconnecting liquid tube, and into the borehole until a constant liquid head is established at the bottom of the borehole, and the one or more hydraulic properties of the medium comprise the saturated hydraulic conductivity of the medium.

8. The apparatus of claim 7, wherein the bottom end of the elongated air tube is a prescribed distance from the bottom of the borehole, the constant liquid head has a height which is equal to said distance, said height is increased by sliding said tube up through the tube cap passageway, and said height is decreased by sliding said tube down through said passageway.

9. The apparatus of claim 7, wherein the elongated liquid tube further comprises a height of 7 feet and an interior diameter of ¾ of an inch, the elongated air tube comprises an interior diameter of ⅛ of an inch and a height which is large enough to allow the elongated air tube to be slidably adjusted to a downward-most position in which the bottom end of the elongated air tube abuts the top surface of the end cap while the top end of the elongated air tube still extends above the top of the tube cap, and the borehole comprises a diameter of 4 inches and a depth of up to 4 feet.

10. The apparatus of claim 2, wherein,
the first liquid weighing subsystem further comprises a removable reservoir cap comprising a reservoir cap passageway between a top of the reservoir cap and a bottom of the reservoir cap,
the reservoir cap is sealably fitted into the opening on the top of the reservoir,
one end of an interconnecting air tube is sealably connected to the reservoir cap passageway,
the first liquid processing subsystem comprises a ring-infiltrating bubbler unit comprising an elongated liquid tube, an infiltration ring, a tube cap comprising a tube cap passageway between a top of the tube cap and a bottom of the tube cap, and an elongated air tube,
the elongated liquid tube comprises a tube passageway between an interior and an exterior of the elongated liquid tube, the tube passageway being located on a side wall of the elongated liquid tube near a top end thereof,
the other end of the interconnecting air tube is sealably connected to the tube passageway,
the tube cap is sealably fitted onto the top end of the elongated liquid tube,
the infiltration ring is axially embedded into the porous medium such that a top end of the infiltration ring either axially extends above a top surface of the medium or is axially flush with the top surface of the medium,
a bottom end of the elongated liquid tube is sealably attached to the top end of the infiltration ring,
the elongated air tube is sealably but slidably inserted into the tube cap passageway such that a bottom end of the elongated air tube extends into the interior of the elongated liquid tube and a top end of the elongated air tube extends above the top of the tube cap,
the top end of the elongated air tube is open to in situ ambient air,
the elongated liquid tube further comprises a base passageway between the interior and the exterior of the elongated liquid tube, the base passageway being located on the side wall of the elongated liquid tube near the bottom end thereof,
the other end of the first interconnecting liquid tube is sealably connected to the base passageway,
the first liquid flows from the hollow interior of the reservoir, through the reservoir passageway, through the first interconnecting liquid tube, through the base passageway, and into an interior of the infiltration ring and the interior of the elongated liquid tube until a constant liquid head is established therein and a constant liquid head pressure is established on the top surface of the medium that is within the interior of the infiltration ring, and
the one or more hydraulic properties of the medium comprise the saturated hydraulic conductivity of the medium that is within the interior of the infiltration ring.

11. The apparatus of claim 10, wherein the elongated liquid tube further comprises a height of 7 feet and an interior diameter of ¾ of an inch, the infiltration ring comprises an interior diameter of 8 inches and a height of 2.5 inches, and the elongated air tube comprises an interior diameter of ⅛ of an inch and a height which is large enough to allow the elongated air tube to be slidably adjusted to a downward-most position in which the bottom end of the elongated air tube abuts the top surface of the medium while the top end of the elongated air tube still extends above the top of the tube cap.

12. The apparatus of claim 2, wherein,
the first liquid weighing subsystem further comprises a removable reservoir cap comprising a reservoir cap passageway between a top of the reservoir cap and a bottom of the reservoir cap,
the reservoir cap is sealably fitted into the opening on the top of the reservoir,
one end of an interconnecting air tube is sealably connected to the reservoir cap passageway,
the first liquid processing subsystem comprises a non-infiltrating bubbler unit and a sorption unit,
the non-infiltrating bubbler unit comprises an elongated liquid tube, a non-porous base, a removable tube cap comprising a tube cap passageway between a top of the tube cap and a bottom of the tube cap, and an elongated air tube,
the elongated liquid tube comprises a tube passageway between an interior and an exterior of the elongated liquid tube, the tube passageway being located on a side wall of the elongated liquid tube near a top end thereof,
the other end of the interconnecting air tube is sealably connected to the tube passageway,
a bottom end of the elongated liquid tube is sealably attached to a top surface of the base such that the base serves to sealably close the bottom end of the elongated liquid tube and also serves to maintain the bubbler unit in a substantially vertical position,
the interior of the elongated liquid tube is partially filled with a second liquid such that a top surface of the second liquid is close to but still beneath the tube passageway,
the tube cap is sealably fitted onto the top end of the elongated liquid tube,
the elongated air tube is sealably but slidably inserted into the tube cap passageway such that a bottom end of the elongated air tube extends a prescribed distance beneath the top surface of the second liquid and a top end of the elongated air tube extends above the top of the tube cap,
the top end of the elongated air tube is open to in situ ambient air,
the sorption unit comprises an infiltration ring, a top cover comprising a cover passageway, and a porous sensing element,
the infiltration ring is disposed on a top surface of the porous medium,
the top cover is sealably attached to the top end of the infiltration ring,
the sensing element comprises a continuous, interconnected system of pores which is permeable to the first liquid, the sensing element is disposed in a space bounded by a bottom surface of the top cover, the top surface of the medium, and an axially inner surface of the infiltration ring, the sensing element being sized and shaped such that it substantially fills said space, the other end of the first interconnecting liquid tube is sealably connected to the cover passageway, the first liquid flows from the hollow interior of the reservoir, through the reservoir passageway, through the first interconnecting liquid tube, through the cover passageway, and into said pores, a bottom surface of the sensing element provides a wetted surface which is in liquid contact with the top surface of the medium such that the first liquid is supplied to the top surface of the medium under a prescribed amount of liquid tension and is sorbed from the sensing element into the top surface of the medium until the first liquid content within the medium and the first liquid content within the sensing element are equalized, and the one or more hydraulic properties of the medium comprise the sorptivity of the medium.

13. The apparatus of claim 12, wherein the amount of liquid tension is increased by sliding the elongated air tube down through the tube cap passageway so as to increase the distance said tube extends beneath the top surface of the second liquid, and the amount of liquid tension is decreased by sliding said tube up through said passageway so as to decrease said distance.

14. The apparatus of claim 12, wherein the porous sensing element comprises a porous ceramic material.

15. The apparatus of claim 12, wherein the elongated liquid tube further comprises a height of 2 feet and an interior diameter of ¾ of an inch, the infiltration ring comprises an interior diameter of 7.8 inches and a height of 4.5 inches, and the elongated air tube comprises an interior diameter of ⅛ of an inch and a height which is large enough to allow the elongated air tube to be slidably adjusted to a downward-most position in which the bottom end of the elongated air tube abuts the top surface of the non-porous base while the top end of the elongated air tube still extends above the top of the removable tube cap.

16. The apparatus of claim 1, further comprising:
an inner infiltration ring which is axially embedded into the porous medium such that a top end of the inner infiltration ring axially extends above a top surface of the medium;
an outer infiltration ring which is axially embedded into the medium such that the outer infiltration ring is substantially concentric with the inner infiltration ring and a top end of the outer infiltration ring axially extends above the top surface of the medium;
a second liquid processing subsystem; and
a second liquid weighing subsystem which stores a second liquid; wherein,
the first liquid weighing subsystem comprises:
a first reservoir comprising: a first hollow interior which is partially filled with the first liquid; an opening on a top of the first reservoir; and a first reservoir passageway between the first hollow interior and an exterior of the first reservoir, wherein the first reservoir passageway is located on a side wall of the first reservoir near a bottom surface of the first hollow interior, and one end of the first interconnecting liquid tube is sealably connected to the first reservoir passageway;
a first removable reservoir cap comprising a first reservoir cap passageway between a top and a bottom of the first removable reservoir cap, wherein the first removable reservoir cap is sealably fitted into the opening on the top of the first reservoir, and one end of a first interconnecting air tube is sealably connected to the first reservoir cap passageway;
a first weighing device comprising a first data port, wherein the first reservoir is centrally disposed on top of the first weighing device, and the first weighing device continuously measures the weight of the first liquid within the first reservoir; and
a first data processing device comprising a second data port, wherein the first and second data ports are interconnected via a first data connection, the first data processing device uses the first data connection to routinely read the weight measurements made by the first weighing device, the first data processing device stores each of said read weight measurements in an time and date stamped format, and the first data processing device analyzes said stored weight measurements on an ongoing basis to determine when a first prescribed steady-state liquid flow rate condition is reached, after which the first data processing device further analyzes said stored weight measurements to compute the saturated hydraulic conductivity of the medium that is within an interior of the inner infiltration ring;
the first liquid processing subsystem comprises a first surface-infiltrating bubbler unit comprising: a first elongated liquid tube; a first dispersive end cap which is perforated to allow the first liquid to flow there-through; a first tube cap comprising a first tube cap passageway between a top and a bottom of the first tube cap; and a first elongated air tube, wherein,
the first elongated liquid tube comprises a first tube passageway between an interior and an exterior of the first elongated liquid tube, the first tube passageway being located on a side wall of the first elongated liquid tube near a top end thereof,
the other end of the first interconnecting air tube is sealably connected to the first tube passageway,
the first tube cap is sealably fitted onto the top end of the first elongated liquid tube,
the first elongated air tube is sealably but slidably inserted into the first tube cap passageway such that a bottom end of the first elongated air tube extends into the interior of the first elongated liquid tube and a top end of the first elongated air tube extends above the top of the first tube cap,
the top end of the first elongated air tube is open to in situ ambient air,
a bottom end of the first elongated liquid tube abuts a top surface of the first dispersive end cap,
the first elongated liquid tube further comprises a first base passageway between the interior and the exterior of the first elongated liquid tube, the first base passageway being located on the side wall of the first elongated liquid tube near the bottom end thereof,
the other end of the first interconnecting liquid tube is sealably connected to the first base passageway,
the first surface-infiltrating bubbler unit is disposed on the top surface of the medium within the interior of the inner infiltration ring such that the first dispersive end cap abuts the top surface of the medium, and
the first liquid flows from the first hollow interior of the first reservoir, through the first reservoir passageway, through the first interconnecting liquid tube, through the first base passageway, into the interior of the first elongated liquid tube, through the first dispersive end cap, and into the interior of the inner infiltration ring until a first constant liquid head is established therein;

the second liquid weighing subsystem comprises:
- a second reservoir comprising: a second hollow interior which is partially filled with the second liquid; an opening on a top of the second reservoir; and a second reservoir passageway between the second hollow interior and an exterior of the second reservoir, wherein the second reservoir passageway is located on a side wall of the second reservoir near a bottom surface of the second hollow interior, and one end of a second interconnecting liquid tube is sealably connected to the second reservoir passageway;
- a second removable reservoir cap comprising a second reservoir cap passageway between a top and a bottom of the second removable reservoir cap, wherein the second removable reservoir cap is sealably fitted into the opening on the top of the second reservoir, and one end of a second interconnecting air tube is sealably connected to the second reservoir cap passageway;
- a second weighing device comprising a third data port, wherein the second reservoir is centrally disposed on top of the second weighing device, and the second weighing device continuously measures the weight of the second liquid within the second reservoir; and
- a second data processing device comprising a fourth data port, wherein the third and fourth data ports are interconnected via a second data connection, the second data processing device uses the second data connection to routinely read the weight measurements made by the second weighing device, the second data processing device stores each of said read weight measurements in an time and date stamped format, and the second data processing device analyzes said stored weight measurements on an ongoing basis to determine when a second prescribed steady-state liquid flow rate condition is reached, after which the second data processing device further analyzes said stored weight measurements to compute the saturated hydraulic conductivity of the medium in a region between the inner and outer infiltration rings; and the second liquid processing subsystem comprises a second surface-infiltrating bubbler unit comprising: a second elongated liquid tube; a second dispersive end cap which is perforated to allow the second liquid to flow there-through; a second tube cap comprising a second tube cap passageway between a top and a bottom of the second tube cap; and a second elongated air tube, wherein,
- the second elongated liquid tube comprises a second tube passageway between an interior and an exterior of the second elongated liquid tube, the second tube passageway being located on a side wall of the second elongated liquid tube near a top end thereof,
- the other end of the second interconnecting air tube is sealably connected to the second tube passageway,
- the second tube cap is sealably fitted onto the top end of the second elongated liquid tube,
- the second elongated air tube is sealably but slidably inserted into the second tube cap passageway such that a bottom end of the second elongated air tube extends into the interior of the second elongated liquid tube and a top end of the second elongated air tube extends above the top of the second tube cap,
- the top end of the second elongated air tube is open to in situ ambient air,
- a bottom end of the second elongated liquid tube abuts a top surface of the second dispersive end cap,
- the second elongated liquid tube further comprises a second base passageway between the interior and the exterior of the second elongated liquid tube, the second base passageway being located on the side wall of the second elongated liquid tube near the bottom end thereof,
- the other end of the second interconnecting liquid tube is sealably connected to the second base passageway,
- the second surface-infiltrating bubbler unit is disposed on the top surface of the medium in said region such that the second dispersive end cap abuts the top surface of the medium, and
- the second liquid flows from the second hollow interior of the second reservoir, through the second reservoir passageway, through the second interconnecting liquid tube, through the second base passageway, into the interior of the second elongated liquid tube, through the second dispersive end cap, and into said region until a second constant liquid head is established in said region.

17. A hydraulic property measurement apparatus, comprising:
- a medium-interfacing means for establishing liquid contact with a porous medium;
- a liquid-sourcing means for storing a liquid and automatically measuring the weight of the stored liquid on an ongoing basis; and
- a liquid-transferring means for sealably interconnecting the medium-interfacing means and the liquid-sourcing means, and allowing the stored liquid to flow through the medium-interfacing means and into the porous medium until the porous medium is saturated, wherein,
- the liquid-sourcing means uses said weight measurements to determine one or more hydraulic properties of the porous medium.

18. An apparatus for testing a porous medium, comprising:
- an interconnecting liquid tube;
- a borehole liquid level stabilization device comprising a floating valve and being adjustably suspended at a prescribed depth within a borehole that is formed in the medium, wherein one end of said tube is sealably connected to the stabilization device;
- a reservoir comprising an opening on a top thereof which is open to in situ ambient air, a hollow interior which is partially filled with a liquid, and a reservoir passageway between said interior and an exterior of the reservoir, wherein,
  - said passageway is located is located on a side wall of the reservoir near a bottom surface of said interior,
  - the other end of said tube is sealably connected to said passageway,
  - the liquid flows from said interior, through said passageway, through said tube, through the stabilization device, and into the borehole until the medium is saturated with the liquid and a constant liquid head having a prescribed height is established at a bottom of the borehole, and
  - the floating valve serves to control the flow rate of the liquid into the borehole in order to maintain the constant liquid head at said height;
- a weighing device comprising a first data port, wherein the reservoir is centrally disposed on top of the weighing device, and the weighing device continuously measures the weight of the liquid within the reservoir;

an elevating device which is used to provide a stable and level platform for the reservoir and weighing device, and is also used to elevate the reservoir to create a prescribed amount of overhead pressure in the apparatus; and a data processing device comprising a second data port and a third data port, wherein, a removable data storage device is connected to the third data port, the first and second data ports are interconnected via a data connection, the data processing device uses the data connection to routinely read the weight measurements made by the weighing device, the data processing device stores each of the read weight measurements in a time and date stamped format, the data processing device analyzes the stored weight measurements on an ongoing basis to compute changes in the amount of the liquid within the reservoir over time, and from said changes the data processing device computes the saturated hydraulic conductivity of the medium.

19. The apparatus of claim 18, wherein the prescribed height of the constant liquid head is increased by decreasing the prescribed depth at which the stabilization device is adjustably suspended within the borehole, and said height is decreased by increasing said depth.

20. The apparatus of claim 18, wherein the stabilization device further comprises an outer diameter of 3 inches, the borehole comprises a diameter of 4 inches and a depth of up to 10 feet, and the prescribed height of the constant liquid head is 3 inches when a bottom of the stabilization device abuts the bottom of the borehole.

21. The apparatus of claim 18, further comprising a pressure regulator unit which is installed along the interconnecting liquid tube near the one end thereof that is sealably connected to the stabilization device, wherein the borehole comprises a depth of up to 50 feet.

* * * * *